United States Patent
Takahashi et al.

(10) Patent No.: US 11,643,458 B2
(45) Date of Patent: May 9, 2023

(54) MONOCLONAL ANTIBODY AGAINST NAV1.7

(71) Applicant: SHIONOGI & CO., LTD., Osaka (JP)

(72) Inventors: Tatsuya Takahashi, Toyonaka (JP); Mai Yoshikawa, Toyonaka (JP); Sosuke Yoneda, Toyonaka (JP); Junji Onoda, Toyonaka (JP); Etsuo Nakamura, Toyonaka (JP); Tsuguo Miyauchi, Toyonaka (JP); Toshiyuki Asaki, Amagasaki (JP); Erika Kasai, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 215 days.

(21) Appl. No.: 17/059,886

(22) PCT Filed: May 30, 2019

(86) PCT No.: PCT/JP2019/021444
§ 371 (c)(1),
(2) Date: Nov. 30, 2020

(87) PCT Pub. No.: WO2019/230856
PCT Pub. Date: Dec. 5, 2019

(65) Prior Publication Data
US 2021/0221876 A1 Jul. 22, 2021

(30) Foreign Application Priority Data
May 31, 2018 (JP) .............................. JP2018-104391

(51) Int. Cl.
| | |
|---|---|
| *A61K 39/395* | (2006.01) |
| *C07K 16/00* | (2006.01) |
| *C07K 16/46* | (2006.01) |
| *C07H 21/04* | (2006.01) |
| *C12N 5/02* | (2006.01) |
| *C12N 1/20* | (2006.01) |
| *C12N 15/00* | (2006.01) |
| *C07K 16/18* | (2006.01) |
| *A61P 29/00* | (2006.01) |
| *A61K 39/00* | (2006.01) |

(52) U.S. Cl.
CPC .............. *C07K 16/18* (2013.01); *A61P 29/00* (2018.01); *A61K 2039/505* (2013.01); *C07K 2317/565* (2013.01); *C07K 2317/64* (2013.01)

(58) Field of Classification Search
None
See application file for complete search history.

(56) References Cited

U.S. PATENT DOCUMENTS

| | | |
|---|---|---|
| 2011/0135662 A1 | 6/2011 | Finney et al. |
| 2014/0342406 A1 | 11/2014 | Finney et al. |
| 2015/0232553 A1 | 8/2015 | Finney et al. |

FOREIGN PATENT DOCUMENTS

| | | |
|---|---|---|
| JP | 2013-507980 A | 3/2013 |
| JP | 2016-512430 A | 4/2016 |
| WO | WO 2011/051350 A1 | 5/2011 |
| WO | WO 2014/159595 A2 | 10/2014 |
| WO | WO 2015/032916 A1 | 3/2015 |
| WO | WO 2015/035173 A1 | 3/2015 |

OTHER PUBLICATIONS

Toledo-Aral, J.J. et al., "Identification of PN1, a predominant voltage-dependent sodium channel expressed principally in peripheral neurons," Proc. Natl. Acad. Sci., vol. 94, Feb. 1997, pp. 1527-1532.
Nassar, M.A. et al., "Nociceptor-specific gene deletion reveals a major role for $Na_v$ 1.7 (PN1) in acute and inflammatory pain," Proc. Natl. Acad. Sci., vol. 101, No. 34, Aug. 24, 2004, pp. 12706-12711.
Goldberg, Y.P. et al., "Treatment of $NA_v$ 1.7-mediated pain in inherited erythromelalgia using a novel sodium channel blocker," Pain, vol. 153, 2012, pp. 80-85.
Zakrzewska, J.M. et al., "Safety and efficacy of a Nav1.7 selective sodium channel blocker in patients with trigeminal neuralgia: a double-blind, placebo-controlled, randomised withdrawal phase 2a trial," The Lancet, vol. 16, Apr. 2017, pp. 291-300.
International Search Report dated Sep. 3, 2019 in PCT/JP2019/021444 filed on May 30, 2019, 2 pages.

*Primary Examiner* — Maher M Haddad
(74) *Attorney, Agent, or Firm* — Oblon, McClelland, Maier & Neustadt, L.L.P.

(57) ABSTRACT

Objective of the present invention is to provide a novel monoclonal antibody against Nav1.7. The present invention discloses a monoclonal antibody against Nav1.7 or its antibody fragment, having specific six CDRs (CDR1 to CDR3 of a heavy chain and CDR1 to CDR3 of a light chain) or specific heavy/light chain variable regions. The monoclonal antibody and the like can be used for treating or preventing pain, pruritus and so on.

20 Claims, 4 Drawing Sheets
Specification includes a Sequence Listing.

Figure 1

| Kabat number | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | CDR1 | | | | | | | | | | | | | | | | | |
| 15C8 VH (SEQ ID NO:14) | | E | V | Q | L | Q | Q | S | G | P | E | L | V | K | P | G | P | S | V | K | I | S | C | K | A | S | G | Y | S | F | T | G | Y | Y | M | H | W | V | K | Q | S | H | G | K | S | L | E | W | I | G |
| 15H6 VH (SEQ ID NO: 18) | | E | V | Q | L | Q | Q | S | G | P | E | L | V | K | P | G | P | S | V | K | I | S | C | K | A | S | G | Y | S | F | T | G | Y | Y | M | H | W | V | K | Q | S | H | G | K | S | L | E | W | I | G |
| 28B5 VH (SEQ ID NO: 20) | | E | V | Q | L | Q | Q | S | G | P | E | L | V | K | L | G | P | S | V | K | I | S | C | K | T | S | G | Y | S | F | T | G | Y | Y | I | H | W | V | K | Q | S | H | G | K | S | L | E | W | I | G |
| 29G3 VH (SEQ ID NO: 23) | | E | V | Q | L | Q | Q | S | G | P | E | L | V | K | P | G | P | S | V | N | I | S | C | K | A | S | G | Y | S | F | T | G | Y | Y | M | H | W | V | K | Q | S | H | G | K | S | L | E | W | I | G |
| | | * | * | * | * | * | * | * | * | * | * | * | * | * | . | * | * | * | * | . | * | * | * | * | . | * | * | * | * | * | * | * | * | * | . | * | * | * | * | * | * | * | * | * | * | * | * | * | * | * |

| Kabat number | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82a | 82b | 82c | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | CDR2 | | | | | | | | | | | | | | | | | | | | | | | | | | | | | | | | | | | | | | | |
| 15C8 VH | L | I | I | — | P | Y | S | G | D | T | F | Y | N | Q | K | F | K | G | K | A | T | L | T | I | D | T | S | S | S | T | A | Y | M | E | I | G | S | L | T | S | E | D | S | A | V | Y | Y | C | A | R |
| 15H6 VH | L | I | I | — | P | Y | S | G | E | I | F | Y | N | Q | K | F | K | G | K | A | T | L | T | V | D | T | S | S | S | T | A | Y | M | E | I | G | S | L | T | S | E | D | S | A | V | Y | Y | C | A | R |
| 28B5 VH | L | I | I | — | P | Y | N | G | D | T | F | Y | N | P | K | F | K | G | K | A | T | L | T | V | D | T | S | S | S | T | V | Y | M | E | L | G | S | L | T | S | E | D | S | A | V | Y | Y | C | A | R |
| 29G3 VH | L | I | I | — | P | Y | N | G | D | T | F | Y | N | Q | K | F | R | G | K | A | T | L | T | V | D | T | S | S | N | T | A | Y | M | A | L | G | S | L | T | S | E | D | S | A | V | Y | Y | C | A | R |
| | * | * | * | . | * | * | . | * | . | . | * | * | * | . | * | * | . | * | * | * | * | * | * | . | * | * | * | * | . | * | . | * | * | . | . | * | * | * | * | * | * | * | * | * | * | * | * | * | * | * |

| Kabat number | 95 | 96 | 97 | 98 | 99 | 100 | 100a | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|
| | | | CDR3 | | | | | | | | | | | | | | | | | |
| 15C8 VH | A | E | V | S | Y | A | M | D | Y | W | G | Q | G | T | S | V | T | V | S | S |
| 15H6 VH | A | E | V | S | Y | A | M | D | Y | W | G | Q | G | T | S | V | T | V | S | S |
| 28B5 VH | A | E | V | S | Y | A | M | D | Y | W | G | Q | G | T | S | V | T | V | S | S |
| 29G3 VH | A | D | V | S | Y | A | M | D | Y | W | G | Q | G | T | S | V | T | V | S | S |
| | * | . | * | * | * | * | * | * | * | * | * | * | * | * | * | * | * | * | * | * |

Figure 2

| Kabat number | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 27c | 27d | 27e | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | | | | | | | | CDR1 |
| 15C8 VK (SEQ ID NO: 43) | | D | V | V | M | T | Q | T | P | L | S | L | P | V | S | L | G | D | Q | A | S | I | S | C | R | S | S | Q | S | L | V | H | S | N | G | N | T | Y | L | H | W | Y | L | Q | K | P | G | Q | S | P |
| 15H6 VK (SEQ ID NO: 44) | | D | V | V | M | T | Q | T | P | L | S | L | P | V | S | L | G | D | Q | A | S | I | S | C | R | S | S | Q | S | L | V | H | S | N | G | N | T | Y | L | H | W | Y | L | Q | R | P | G | Q | S | P |
| 28B5 VK (SEQ ID NO: 46) | | D | V | V | M | T | Q | T | P | L | S | L | P | V | S | L | G | D | Q | A | S | I | S | C | R | S | S | Q | S | L | V | H | S | N | G | N | T | Y | L | H | W | Y | L | Q | K | P | G | Q | S | P |
| 29G3 VK (SEQ ID NO: 48) | | D | V | V | M | T | Q | T | P | L | S | L | P | V | S | L | G | D | Q | A | S | L | S | C | R | S | S | Q | S | L | V | H | S | N | G | N | T | Y | L | H | W | Y | L | Q | K | P | G | Q | S | P |
| | | * | * | * | * | * | * | * | * | * | * | * | * | * | * | * | * | * | * | * | * | . | * | * | * | * | * | * | * | * | * | * | * | * | * | * | * | * | * | * | * | * | * | . | * | * | * | * | * | * |

| Kabat number | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | CDR2 | | | | | | | | | | | | | | | | | | | | | | | | | | | | | | | | | | | | | | | | | | | CDR3 | |
| 15C8 VK | K | L | L | I | Y | K | V | S | N | R | F | S | G | V | P | D | R | F | S | G | S | G | S | G | T | D | F | T | L | K | I | S | R | V | E | A | E | D | L | G | V | Y | F | C | S | Q | S | T | H | V |
| 15H6 VK | K | L | L | I | Y | K | V | S | N | R | F | S | G | V | P | D | R | F | S | G | S | G | S | G | T | D | F | K | F | K | I | S | R | V | E | A | E | D | L | G | V | Y | F | C | S | Q | S | T | H | V |
| 28B5 VK | K | L | L | I | Y | K | V | S | N | R | I | S | G | V | P | D | R | F | S | G | S | G | S | G | T | D | F | T | L | K | I | S | R | V | E | A | E | D | L | G | V | Y | F | C | S | Q | S | I | H | V |
| 29G3 VK | K | L | L | I | Y | K | V | S | N | R | F | S | G | V | P | D | R | F | S | G | S | G | S | G | T | D | F | T | L | K | I | S | R | V | E | A | E | D | L | G | V | Y | F | C | S | Q | S | T | H | V |
| | * | * | * | * | * | * | * | * | * | * | . | * | * | * | * | * | * | * | * | * | * | * | * | * | * | * | * | . | . | * | * | * | * | * | * | * | * | * | * | * | * | * | * | * | * | * | * | . | * | * |

| Kabat number | 95 | 96 | 97 | 98 | 99 | 100 | 101 | 102 | 103 | 104 | 105 | 106 | 107 | 108 |
|---|---|---|---|---|---|---|---|---|---|---|---|---|---|---|
| 15C8 VK | P | F | T | F | G | S | G | T | K | L | E | I | K | R |
| 15H6 VK | P | F | T | F | G | G | G | T | K | L | E | I | K | R |
| 28B5 VK | P | W | T | F | G | G | G | T | K | L | E | I | K | R |
| 29G3 VK | P | F | T | F | G | S | G | T | K | L | E | I | K | R |
| | * | . | . | * | * | . | * | * | * | * | * | * | * | * |

Figure 3A

```
                    1  2  3  4  5  6  7  8  9 10 11 12 13 14 15 16 17 18 19 20 21 22 23 24 25 26 27 28 29 30 31 32 33 34 35 36 37 38 39 40 41 42 43 44 45 46 47 48 49
h12H4 VH
(SEQ ID NO: 52)     Q  V  Q  L  V  Q  S  G  A  E  V  K  K  P  G  A  S  V  K  V  S  C  K  V  S  G  Y  T  F  T  Y  Y  Y  I  Q  W  V  R  Q  A  P  G  Q  G  L  E  W  M  G
                                                                                                    CDR1 (SEQ ID NO: 27)
```

```
Kabat number   50 51 52 52a 53 54 55 56 57 58 59 60 61 62 63 64 65 66 67 68 69 70 71 72 73 74 75 76 77 78 79 80 81 82 82a 82b 82c 83 84 85 86 87 88 89
h12H4 VH        W  I  Y  P  G  N  G  N  S  N  I  T  E  K  F  K  G  R  V  T  M  T  T  D  T  S  T  S  T  A  Y  M  E  L  R  S  L  R  S  D  D  T  A  V
                        CDR2 (SEQ ID NO: 28)
```

```
Kabat number   90 91 92 93 94 95 96 97 98 99 100 100a 101 102 103 104 105 106 107 108 109 110 111 112 113
h12H4 VH        Y  Y  C  A  R  I  F  T  T  M  V   G   D   Y   W   G   Q   G   T   T   V   T   V   S   S
                        CDR3 (SEQ ID NO: 29)
```

Figure 3B

```
                    1  2  3  4  5  6  7  8  9 10 11 12 13 14 15 16 17 18 19 20 21 22 23 24 25 26 27 27a 27b 27c 27d 27e 28 29 30 31 32 33 34 35 36 37 38 39 40 41 42 43 44
h12H4 VK
(SEQ ID NO: 53)     D  V  V  M  T  Q  S  P  L  S  L  P  V  T  L  G  Q  P  A  S  I  S  C  R  S  S  Q  S   L   V   H   S  N  G  N  T  Y  L  H  W  F  Q  Q  R  P  G  Q  S  P
                                                                                                          CDR1 (SEQ ID NO: 34)
```

```
Kabat number   45 46 47 48 49 50 51 52 53 54 55 56 57 58 59 60 61 62 63 64 65 66 67 68 69 70 71 72 73 74 75 76 77 78 79 80 81 82 83 84 85 86 87 88
h12H4 VK        R  R  L  I  Y  K  V  S  N  R  F  S  G  V  P  D  R  F  S  G  S  G  S  G  T  D  F  T  L  K  I  S  R  V  E  A  E  D  V  G  V  Y  Y  C
                        CDR2 (SEQ ID NO: 35)
```

```
Kabat number   89 90 91 92 93 94 95 96 97 98 99 100 101 102 103 104 105 106 107 108 109
h12H4 VK        S  Q  S  T  H  V  P  W  T  F  G  G   G   T   K   V   E   I   K   R   T
                        CDR3 (SEQ ID NO: 50)
``` n=8 or 9, **$p$ <0.01 vs vehicle

Time after treatment (hours)    N=7, **$p$ <0.01 v.s vehicle

SEQUENCE LISTING

```
<160> NUMBER OF SEQ ID NOS: 64

<210> SEQ ID NO 1
<211> LENGTH: 14
<212> TYPE: PRT
<213> ORGANISM: Artificial sequence
<220> FEATURE:
<223> OTHER INFORMATION: hCE3C peptide

<400> SEQUENCE: 1

Ser Val Asn Val Asp Lys Gln Pro Lys Tyr Glu Tyr Ser Leu
1               5                   10

<210> SEQ ID NO 2
<211> LENGTH: 118
<212> TYPE: PRT
<213> ORGANISM: Artificial sequence
<220> FEATURE:
<223> OTHER INFORMATION: Heavy chain of 3B2

<400> SEQUENCE: 2

Glu Val Gln Leu Val Glu Ser Gly Gly Gly Leu Val Lys Pro Gly Gly
1               5                   10                  15

Ser Leu Lys Leu Ser Cys Ala Ala Thr Gly Phe Thr Phe Ser Trp Tyr
            20                  25                  30

Val Met Ser Trp Val Arg Gln Thr Pro Ala Lys Arg Leu Glu Trp Val
        35                  40                  45

Ala Thr Ile Ser Ser Gly Gly Val Ser Thr Tyr Tyr Pro Asp Thr Met
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Gly Met Tyr Tyr Cys
                85                  90                  95
```

Ala Arg Leu Trp Asp Pro Tyr Ala Met Asp Tyr Trp Gly Gln Gly Thr
            100                 105                 110

Ser Val Thr Val Ser Ser
        115

<210> SEQ ID NO 3
<211> LENGTH: 5
<212> TYPE: PRT
<213> ORGANISM: Artificial sequence
<220> FEATURE:
<223> OTHER INFORMATION: CDR1 of 3B2 VH

<400> SEQUENCE: 3

Trp Tyr Val Met Ser
1               5

<210> SEQ ID NO 4
<211> LENGTH: 17
<212> TYPE: PRT
<213> ORGANISM: Artificial sequence
<220> FEATURE:
<223> OTHER INFORMATION: CDR2 of 3B2 VH

<400> SEQUENCE: 4

Thr Ile Ser Ser Gly Gly Val Ser Thr Tyr Tyr Pro Asp Thr Met Lys
1               5                   10                  15

Gly

<210> SEQ ID NO 5
<211> LENGTH: 9
<212> TYPE: PRT
<213> ORGANISM: Artificial sequence
<220> FEATURE:
<223> OTHER INFORMATION: CDR3 of 3B2 VH

<400> SEQUENCE: 5

Leu Trp Asp Pro Tyr Ala Met Asp Tyr
1               5

<210> SEQ ID NO 6
<211> LENGTH: 121
<212> TYPE: PRT
<213> ORGANISM: Artificial sequence
<220> FEATURE:
<223> OTHER INFORMATION: Heavy chain of 5E12

<400> SEQUENCE: 6

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Ile Tyr Asp Ser Lys Phe
    50                  55                  60

Gln Gly Lys Ala Thr Ile Thr Ala Asp Thr Ser Ser Asn Thr Ala Tyr
65                  70                  75                  80

Met Gln Leu Ser Ser Leu Thr Ser Gly Asp Thr Ala Val Tyr Tyr Cys
                85                  90                  95

Ala Arg Val Tyr Asp Gly Asn Tyr Val Gly Ala Met Asp Tyr Trp Gly
            100                 105                 110

```
Gln Gly Thr Ser Val Thr Val Ser Ser
        115                 120

<210> SEQ ID NO 7
<211> LENGTH: 5
<212> TYPE: PRT
<213> ORGANISM: Artificial sequence
<220> FEATURE:
<223> OTHER INFORMATION: CDR1 of 5E12 VH

<400> SEQUENCE: 7

Asp Thr Tyr Met His
1               5

<210> SEQ ID NO 8
<211> LENGTH: 17
<212> TYPE: PRT
<213> ORGANISM: Artificial sequence
<220> FEATURE:
<223> OTHER INFORMATION: CDR2 of 5E12 VH

<400> SEQUENCE: 8

Arg Ile Asp Pro Ala Asn Gly Asn Thr Ile Tyr Asp Ser Lys Phe Gln
1               5                   10                  15

Gly

<210> SEQ ID NO 9
<211> LENGTH: 12
<212> TYPE: PRT
<213> ORGANISM: Artificial sequence
<220> FEATURE:
<223> OTHER INFORMATION: CDR3 of 5E12 VH

<400> SEQUENCE: 9

Val Tyr Asp Gly Asn Tyr Val Gly Ala Met Asp Tyr
1               5                   10

<210> SEQ ID NO 10
<211> LENGTH: 121
<212> TYPE: PRT
<213> ORGANISM: Artificial sequence
<220> FEATURE:
<223> OTHER INFORMATION: Heavy chain of 7B9

<400> SEQUENCE: 10

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Arg Gln Arg Pro Glu Gln Gly Leu Glu Trp Ile
        35                  40                  45

Gly Arg Ile Asp Pro Ala Asn Gly Asn Thr Ile Tyr Ala Ser Lys Phe
    50                  55                  60

Gln Gly Lys Ala Thr Ile Thr Ala Asp Thr Ser Ser Asn Thr Ala Tyr
65                  70                  75                  80

Ile Gln Phe Thr Ser Leu Thr Ser Gly Asp Thr Ala Val Tyr Tyr Cys
                85                  90                  95

Ala Arg Val Asp Asp Gly Asn Tyr Val Gly Ala Met Asp Tyr Trp Gly
            100                 105                 110

Gln Gly Thr Ser Val Thr Val Ser Ser
        115                 120
```

<210> SEQ ID NO 11
<211> LENGTH: 5
<212> TYPE: PRT
<213> ORGANISM: Artificial sequence
<220> FEATURE:
<223> OTHER INFORMATION: CDR1 of 7B9 VH

<400> SEQUENCE: 11

Asp Thr Tyr Ile His
1               5

<210> SEQ ID NO 12
<211> LENGTH: 17
<212> TYPE: PRT
<213> ORGANISM: Artificial sequence
<220> FEATURE:
<223> OTHER INFORMATION: CDR2 of 7B9 VH

<400> SEQUENCE: 12

Arg Ile Asp Pro Ala Asn Gly Asn Thr Ile Tyr Ala Ser Lys Phe Gln
1               5                   10                  15

Gly

<210> SEQ ID NO 13
<211> LENGTH: 12
<212> TYPE: PRT
<213> ORGANISM: Artificial sequence
<220> FEATURE:
<223> OTHER INFORMATION: CDR3 of 7B9 VH

<400> SEQUENCE: 13

Val Asp Asp Gly Asn Tyr Val Gly Ala Met Asp Tyr
1               5                   10

<210> SEQ ID NO 14
<211> LENGTH: 118
<212> TYPE: PRT
<213> ORGANISM: Artificial sequence
<220> FEATURE:
<223> OTHER INFORMATION: Heavy chain of 15C8

<400> SEQUENCE: 14

Glu Val Gln Leu Gln Gln Ser Gly Pro Glu Leu Val Lys Pro Gly Pro
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser His Gly Lys Ser Leu Glu Trp Ile
            35                  40                  45

Gly Leu Ile Ile Pro Tyr Ser Gly Asp Thr Phe Tyr Asn Gln Lys Phe
    50                  55                  60

Lys Gly Lys Ala Thr Leu Thr Ile Asp Thr Ser Ser Thr Ala Tyr
65                  70                  75                  80

Met Glu Ile Gly Ser Leu Thr Ser Glu Asp Ser Ala Val Tyr Tyr Cys
                85                  90                  95

Ala Arg Ala Glu Val Ser Tyr Ala Met Asp Tyr Trp Gly Gln Gly Thr
            100                 105                 110

Ser Val Thr Val Ser Ser
        115

<210> SEQ ID NO 15
<211> LENGTH: 5
<212> TYPE: PRT
<213> ORGANISM: Artificial sequence

```
<220> FEATURE:
<223> OTHER INFORMATION: CDR1 of 15C8 VH, 15H6 VH and 29G3 VH

<400> SEQUENCE: 15

Gly Tyr Tyr Met His
1               5

<210> SEQ ID NO 16
<211> LENGTH: 17
<212> TYPE: PRT
<213> ORGANISM: Artificial sequence
<220> FEATURE:
<223> OTHER INFORMATION: CDR2 of 15C8 VH

<400> SEQUENCE: 16

Leu Ile Ile Pro Tyr Ser Gly Asp Thr Phe Tyr Asn Gln Lys Phe Lys
1               5                   10                  15

Gly

<210> SEQ ID NO 17
<211> LENGTH: 9
<212> TYPE: PRT
<213> ORGANISM: Artificial sequence
<220> FEATURE:
<223> OTHER INFORMATION: CDR3 of 15C8 VH, 15H6 VH and 28B5 VH

<400> SEQUENCE: 17

Ala Glu Val Ser Tyr Ala Met Asp Tyr
1               5

<210> SEQ ID NO 18
<211> LENGTH: 118
<212> TYPE: PRT
<213> ORGANISM: Artificial sequence
<220> FEATURE:
<223> OTHER INFORMATION: Heavy chain of 15H6

<400> SEQUENCE: 18

Glu Val Gln Leu Gln Gln Ser Gly Pro Glu Leu Val Lys Pro Gly Pro
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser His Gly Lys Ser Leu Glu Trp Ile
            35                  40                  45

Gly Leu Ile Ile Pro Tyr Ser Gly Glu Ile Phe Tyr Asn Gln Lys Phe
        50                  55                  60

Lys Gly Lys Ala Thr Leu Thr Val Asp Thr Ser Ser Thr Ala Tyr
65                  70                  75                  80

Met Glu Ile Gly Ser Leu Thr Ser Glu Asp Ser Ala Val Tyr Tyr Cys
                85                  90                  95

Ala Arg Ala Glu Val Ser Tyr Ala Met Asp Tyr Trp Gly Gln Gly Thr
            100                 105                 110

Ser Val Thr Val Ser Ser
        115

<210> SEQ ID NO 19
<211> LENGTH: 17
<212> TYPE: PRT
<213> ORGANISM: Artificial sequence
<220> FEATURE:
<223> OTHER INFORMATION: CDR2 of 15H6 VH

<400> SEQUENCE: 19
```

Leu Ile Ile Pro Tyr Ser Gly Glu Ile Phe Tyr Asn Gln Lys Phe Lys
1               5                   10                  15

Gly

<210> SEQ ID NO 20
<211> LENGTH: 118
<212> TYPE: PRT
<213> ORGANISM: Artificial sequence
<220> FEATURE:
<223> OTHER INFORMATION: Heavy chain of 28B5

<400> SEQUENCE: 20

Glu Val Gln Leu Gln Gln Ser Gly Pro Glu Leu Val Lys Leu Gly Pro
1               5                   10                  15

Ser Val Lys Ile Ser Cys Lys Thr Ser Gly Tyr Ser Phe Thr Gly Tyr
            20                  25                  30

Tyr Ile His Trp Val Lys Gln Ser His Gly Lys Ser Leu Glu Trp Ile
        35                  40                  45

Gly Leu Ile Ile Pro Tyr Asn Gly Asp Thr Phe Tyr Asn Pro Lys Phe
    50                  55                  60

Lys Gly Lys Ala Thr Leu Thr Val Asp Thr Ser Ser Ser Thr Val Tyr
65                  70                  75                  80

Met Glu Leu Gly Ser Leu Thr Ser Glu Asp Ser Ala Val Tyr Tyr Cys
                85                  90                  95

Ala Arg Ala Glu Val Ser Tyr Ala Met Asp Tyr Trp Gly Gln Gly Thr
            100                 105                 110

Ser Val Thr Val Ser Ser
        115

<210> SEQ ID NO 21
<211> LENGTH: 5
<212> TYPE: PRT
<213> ORGANISM: Artificial sequence
<220> FEATURE:
<223> OTHER INFORMATION: CDR1 of 28B5 VH

<400> SEQUENCE: 21

Gly Tyr Tyr Ile His
1               5

<210> SEQ ID NO 22
<211> LENGTH: 17
<212> TYPE: PRT
<213> ORGANISM: Artificial sequence
<220> FEATURE:
<223> OTHER INFORMATION: CDR2 of 28B5 VH

<400> SEQUENCE: 22

Leu Ile Ile Pro Tyr Asn Gly Asp Thr Phe Tyr Asn Pro Lys Phe Lys
1               5                   10                  15

Gly

<210> SEQ ID NO 23
<211> LENGTH: 118
<212> TYPE: PRT
<213> ORGANISM: Artificial sequence
<220> FEATURE:
<223> OTHER INFORMATION: Heavy chain of 29G3

<400> SEQUENCE: 23

Glu Val Gln Leu Gln Gln Ser Gly Pro Glu Leu Val Lys Pro Gly Pro

```
                1               5                  10                  15
            Ser Val Asn Ile Ser Cys Lys Ala Ser Gly Tyr Ser Phe Thr Gly Tyr
                            20                  25                  30

Tyr Met His Trp Val Lys Gln Ser His Gly Lys Ser Leu Glu Trp Ile
                            35                  40                  45

Gly Leu Ile Ile Pro Tyr Asn Gly Asp Thr Phe Tyr Asn Gln Lys Phe
                    50                  55                  60

Arg Gly Lys Ala Thr Leu Thr Val Asp Thr Ser Ser Asn Thr Ala Tyr
            65                  70                  75                  80

Met Ala Leu Gly Ser Leu Thr Ser Glu Asp Ser Ala Val Tyr Tyr Cys
                            85                  90                  95

Ala Arg Ala Asp Val Ser Tyr Ala Met Asp Tyr Trp Gly Gln Gly Thr
                        100                 105                 110

Ser Val Thr Val Ser Ser
                    115
```

<210> SEQ ID NO 24
<211> LENGTH: 17
<212> TYPE: PRT
<213> ORGANISM: Artificial sequence
<220> FEATURE:
<223> OTHER INFORMATION: CDR2 of 29G3 VH

<400> SEQUENCE: 24

```
            Leu Ile Ile Pro Tyr Asn Gly Asp Thr Phe Tyr Asn Gln Lys Phe Arg
            1               5                  10                  15

Gly
```

<210> SEQ ID NO 25
<211> LENGTH: 9
<212> TYPE: PRT
<213> ORGANISM: Artificial sequence
<220> FEATURE:
<223> OTHER INFORMATION: CDR3 of 29G3 VH

<400> SEQUENCE: 25

```
            Ala Asp Val Ser Tyr Ala Met Asp Tyr
            1               5
```

<210> SEQ ID NO 26
<211> LENGTH: 118
<212> TYPE: PRT
<213> ORGANISM: Artificial sequence
<220> FEATURE:
<223> OTHER INFORMATION: Heavy chain of 12H4

<400> SEQUENCE: 26

```
            Gln Val Gln Leu Gln Gln Ser Gly Pro Glu Leu Val Lys Pro Gly Ala
            1               5                  10                  15

Ser Val Arg Ile Ser Cys Lys Val Ser Gly Tyr Thr Phe Thr Tyr Tyr
                            20                  25                  30

Tyr Ile Gln Trp Val Lys Gln Arg Pro Gly Gln Gly Leu Glu Trp Ile
                            35                  40                  45

Gly Trp Ile Tyr Pro Gly Asn Gly Asn Ser Asn Ile Thr Glu Lys Phe
                    50                  55                  60

Lys Gly Lys Ala Thr Leu Thr Ala Asp Ser Ser Ser Thr Ala Tyr
            65                  70                  75                  80

Met Gln Leu Ser Ser Leu Thr Ser Glu Asp Ser Ala Glu Tyr Phe Cys
                            85                  90                  95
```

Ala Arg Ile Phe Thr Thr Met Val Gly Asp Tyr Trp Gly Gln Gly Thr
            100                 105                 110

Thr Leu Thr Val Ser Ser
        115

<210> SEQ ID NO 27
<211> LENGTH: 5
<212> TYPE: PRT
<213> ORGANISM: Artificial sequence
<220> FEATURE:
<223> OTHER INFORMATION: CDR1 of 12H4 VH, h12H4 VH, h12H4-2 VH and
      h12H4-3 VH

<400> SEQUENCE: 27

Tyr Tyr Tyr Ile Gln
1               5

<210> SEQ ID NO 28
<211> LENGTH: 17
<212> TYPE: PRT
<213> ORGANISM: Artificial sequence
<220> FEATURE:
<223> OTHER INFORMATION: CDR2 of 12H4 VH, h12H4 VH, h12H4-2 VH and
      h12H4-3 VH

<400> SEQUENCE: 28

Trp Ile Tyr Pro Gly Asn Gly Asn Ser Asn Ile Thr Glu Lys Phe Lys
1               5                   10                  15

Gly

<210> SEQ ID NO 29
<211> LENGTH: 9
<212> TYPE: PRT
<213> ORGANISM: Artificial sequence
<220> FEATURE:
<223> OTHER INFORMATION: CDR3 of 12H4 VH, 22D3 VH, h12H4 VH, h12H4-2 VH
      and h12H4-3 VH

<400> SEQUENCE: 29

Ile Phe Thr Thr Met Val Gly Asp Tyr
1               5

<210> SEQ ID NO 30
<211> LENGTH: 118
<212> TYPE: PRT
<213> ORGANISM: Artificial sequence
<220> FEATURE:
<223> OTHER INFORMATION: Heavy chain of 22D3

<400> SEQUENCE: 30

Gln Val Gln Leu Gln Gln Ser Gly Pro Glu Leu Val Lys Pro Gly Ala
1               5                   10                  15

Ser Val Arg Ile Ser Cys Lys Val Ser Gly Tyr Thr Phe Thr His Tyr
                20                  25                  30

Tyr Ile Gln Trp Val Lys Gln Arg Pro Gly Gln Gly Leu Glu Trp Ile
            35                  40                  45

Gly Trp Ile Tyr Pro Gly Asn Gly Asn Thr Asn Asn Thr Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ile Phe Thr Thr Met Val Gly Asp Tyr Trp Gly Gln Gly Thr

Thr Leu Thr Val Ser Ser
            115

<210> SEQ ID NO 31
<211> LENGTH: 5
<212> TYPE: PRT
<213> ORGANISM: Artificial sequence
<220> FEATURE:
<223> OTHER INFORMATION: CDR1 of 22D3 VH

<400> SEQUENCE: 31

His Tyr Tyr Ile Gln
1               5

<210> SEQ ID NO 32
<211> LENGTH: 17
<212> TYPE: PRT
<213> ORGANISM: Artificial sequence
<220> FEATURE:
<223> OTHER INFORMATION: CDR2 of 22D3 VH

<400> SEQUENCE: 32

Trp Ile Tyr Pro Gly Asn Gly Asn Thr Asn Thr Glu Lys Phe Lys
1               5                   10                  15

Gly

<210> SEQ ID NO 33
<211> LENGTH: 113
<212> TYPE: PRT
<213> ORGANISM: Artificial sequence
<220> FEATURE:
<223> OTHER INFORMATION: Light chain of 3B2

<400> SEQUENCE: 33

Asp Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Val Pro Phe Thr Phe Gly Ser Gly Thr Lys Leu Glu Ile Lys
            100                 105                 110

Arg

<210> SEQ ID NO 34
<211> LENGTH: 16
<212> TYPE: PRT
<213> ORGANISM: Artificial sequence
<220> FEATURE:
<223> OTHER INFORMATION: CDR1 of 3B2 VK, 15C8 VK, 15H6 VK, 28B5 VK, 29G3
      VK, 12H4 VK, 22D3 VK, h12H4 VK, h12H4-2 VK and h12H4-3 VK

<400> SEQUENCE: 34

Arg Ser Ser Gln Ser Leu Val His Ser Asn Gly Asn Thr Tyr Leu His
1               5                   10                  15

<210> SEQ ID NO 35
<211> LENGTH: 7
<212> TYPE: PRT
<213> ORGANISM: Artificial sequence
<220> FEATURE:
<223> OTHER INFORMATION: CDR2 of 3B2 VK, 15C8 VK, 28B5 VK, 29G3 VK, 12H4
    VK, 22D3VK, h12H4 VK, h12H4-2 VK and h12H4-3 VK

<400> SEQUENCE: 35

Lys Val Ser Asn Arg Phe Ser
1               5

<210> SEQ ID NO 36
<211> LENGTH: 9
<212> TYPE: PRT
<213> ORGANISM: Artificial sequence
<220> FEATURE:
<223> OTHER INFORMATION: CDR3 of 3B2 VK, 15C8 VK, 15H6 VK and 29G3 VK

<400> SEQUENCE: 36

Ser Gln Ser Thr His Val Pro Phe Thr
1               5

<210> SEQ ID NO 37
<211> LENGTH: 108
<212> TYPE: PRT
<213> ORGANISM: Artificial sequence
<220> FEATURE:
<223> OTHER INFORMATION: Light chain of 5E12

<400> SEQUENCE: 37

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Gly Phe Thr Leu Asn Ile Asn Ser Val Glu Thr
65                  70                  75                  80

Glu Asp Phe Gly Met Tyr Phe Cys Gln Gln Ser Asn Tyr Trp Pro Phe
                85                  90                  95

Thr Phe Gly Ser Gly Thr Lys Leu Arg Ile Lys Arg
            100                 105

<210> SEQ ID NO 38
<211> LENGTH: 11
<212> TYPE: PRT
<213> ORGANISM: Artificial sequence
<220> FEATURE:
<223> OTHER INFORMATION: CDR1 of 5E12 VK and 7B9 VK

<400> SEQUENCE: 38

Arg Ala Ser Gln Ser Ile Ser Asn Asn Leu His
1               5                   10

<210> SEQ ID NO 39
<211> LENGTH: 7
<212> TYPE: PRT
<213> ORGANISM: Artificial sequence
<220> FEATURE:
<223> OTHER INFORMATION: CDR2 of 5E12 VK

<400> SEQUENCE: 39

Tyr Ala Ser Gln Ser Ile Ser
1               5

<210> SEQ ID NO 40
<211> LENGTH: 9
<212> TYPE: PRT
<213> ORGANISM: Artificial sequence
<220> FEATURE:
<223> OTHER INFORMATION: CDR3 of 5E12 VK and 7B9 VK

<400> SEQUENCE: 40

Gln Gln Ser Asn Tyr Trp Pro Phe Thr
1               5

<210> SEQ ID NO 41
<211> LENGTH: 108
<212> TYPE: PRT
<213> ORGANISM: Artificial sequence
<220> FEATURE:
<223> OTHER INFORMATION: Light chain of 7B9 VK

<400> SEQUENCE: 41

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Thr Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Tyr Trp Pro Phe
                85                  90                  95

Thr Phe Gly Ser Gly Thr Lys Leu Gly Ile Lys Arg
            100                 105

<210> SEQ ID NO 42
<211> LENGTH: 7
<212> TYPE: PRT
<213> ORGANISM: Artificial sequence
<220> FEATURE:
<223> OTHER INFORMATION: CDR2 of 7B9 VK

<400> SEQUENCE: 42

Tyr Thr Ser Gln Ser Ile Ser
1               5

<210> SEQ ID NO 43
<211> LENGTH: 113
<212> TYPE: PRT
<213> ORGANISM: Artificial sequence
<220> FEATURE:
<223> OTHER INFORMATION: Light chain of 15C8

<400> SEQUENCE: 43

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

```
Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
                100                 105                 110

Arg
```

<210> SEQ ID NO 44
<211> LENGTH: 113
<212> TYPE: PRT
<213> ORGANISM: Artificial sequence
<220> FEATURE:
<223> OTHER INFORMATION: Light chain of 15H6

<400> SEQUENCE: 44

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                 20                  25                  30

Asn Gly Asn Thr Tyr Leu His Trp Tyr Leu Gln Arg Pro Gly Gln Ser
            35                  40                  45

Pro Lys Leu Leu Ile Tyr Lys Val Ser Asn Arg Ile Ser Gly Val Pro
 50                  55                  60

Asp Arg Phe Ser Gly Ser Gly Ser Gly Thr Asp Phe Lys Phe Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
                100                 105                 110

Arg
```

<210> SEQ ID NO 45
<211> LENGTH: 7
<212> TYPE: PRT
<213> ORGANISM: Artificial sequence
<220> FEATURE:
<223> OTHER INFORMATION: CDR2 of 15H6 VK

<400> SEQUENCE: 45

```
Lys Val Ser Asn Arg Ile Ser
 1               5
```

<210> SEQ ID NO 46
<211> LENGTH: 113
<212> TYPE: PRT
<213> ORGANISM: Artificial sequence
<220> FEATURE:
<223> OTHER INFORMATION: Light chain of 28B5

<400> SEQUENCE: 46

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                 20                  25                  30
```

-continued

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Ile His Val Pro Trp Thr Phe Gly Gly Gly Thr Lys Leu Glu Ile Lys
            100                 105                 110

Arg

<210> SEQ ID NO 47
<211> LENGTH: 9
<212> TYPE: PRT
<213> ORGANISM: Artificial sequence
<220> FEATURE:
<223> OTHER INFORMATION: CDR3 of 28B5 VK

<400> SEQUENCE: 47

Ser Gln Ser Ile His Val Pro Trp Thr
1               5

<210> SEQ ID NO 48
<211> LENGTH: 113
<212> TYPE: PRT
<213> ORGANISM: Artificial sequence
<220> FEATURE:
<223> OTHER INFORMATION: Light chain of 29G3

<400> SEQUENCE: 48

Asp Val Val Met Thr Gln Thr Pro Leu Ser Leu Pro Val Ser Leu Gly
1               5                   10                  15

Asp Gln Ala Ser Leu Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
            100                 105                 110

Arg

<210> SEQ ID NO 49
<211> LENGTH: 113
<212> TYPE: PRT
<213> ORGANISM: Artificial sequence
<220> FEATURE:
<223> OTHER INFORMATION: Light chain of 12H4

<400> SEQUENCE: 49

Asp Val Val Met Thr Gln Ala Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

```
Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Thr Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
                100                 105                 110

Arg
```

<210> SEQ ID NO 50
<211> LENGTH: 9
<212> TYPE: PRT
<213> ORGANISM: Artificial sequence
<220> FEATURE:
<223> OTHER INFORMATION: CDR3 of 12H4 VK, h12H4 VK, h12H4-2 VK and
      h12H4-3 VK

<400> SEQUENCE: 50

```
Ser Gln Ser Thr His Val Pro Trp Thr
 1               5
```

<210> SEQ ID NO 51
<211> LENGTH: 113
<212> TYPE: PRT
<213> ORGANISM: Artificial sequence
<220> FEATURE:
<223> OTHER INFORMATION: Light chain of 22D3

<400> SEQUENCE: 51

```
Asp Val Val Met Thr Gln Ala Pro Leu Ser Leu Pro Val Ser Leu Gly
 1               5                  10                  15

Asp Gln Ala Ser Ile Ser Cys Arg Ser Ser Gln Ser Leu Val His Ser
                 20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Trp Thr Phe Gly Gly Gly Thr Lys Leu Glu Ile Lys
                100                 105                 110

Arg
```

<210> SEQ ID NO 52
<211> LENGTH: 118
<212> TYPE: PRT
<213> ORGANISM: Artificial sequence
<220> FEATURE:
<223> OTHER INFORMATION: Heavy chain of h12H4

<400> SEQUENCE: 52

```
Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Phe Thr Tyr Tyr
                 20                  25                  30
```

```
Tyr Ile Gln Trp Val Arg Gln Ala Pro Gly Gln Gly Leu Glu Trp Met
            35                  40                  45

Gly Trp Ile Tyr Pro Gly Asn Gly Asn Ser Asn Ile Thr Glu Lys Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Ile Phe Thr Thr Met Val Gly Asp Tyr Trp Gly Gln Gly Thr
            100                 105                 110

Thr Val Thr Val Ser Ser
            115

<210> SEQ ID NO 53
<211> LENGTH: 114
<212> TYPE: PRT
<213> ORGANISM: Artificial sequence
<220> FEATURE:
<223> OTHER INFORMATION: Light chain of h12H4 and h12H4-2

<400> SEQUENCE: 53

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
            35                  40                  45

Pro Arg Arg Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
            100                 105                 110

Arg Thr

<210> SEQ ID NO 54
<211> LENGTH: 7
<212> TYPE: PRT
<213> ORGANISM: Artificial sequence
<220> FEATURE:
<223> OTHER INFORMATION: CDR2 of VK
<220> FEATURE:
<221> NAME/KEY: misc_feature
<222> LOCATION: (6)..(6)
<223> OTHER INFORMATION: Xaa can be Ile or Phe

<400> SEQUENCE: 54

Lys Val Ser Asn Arg Xaa Ser
 1               5

<210> SEQ ID NO 55
<211> LENGTH: 9
<212> TYPE: PRT
<213> ORGANISM: Artificial sequence
<220> FEATURE:
<223> OTHER INFORMATION: CDR3 of VK
<220> FEATURE:
<221> NAME/KEY: misc_feature
<222> LOCATION: (4)..(4)
```

```
<223> OTHER INFORMATION: Xaa can be Thr or Ile
<220> FEATURE:
<221> NAME/KEY: misc_feature
<222> LOCATION: (8)..(8)
<223> OTHER INFORMATION: Xaa can be Phe or Trp

<400> SEQUENCE: 55

Ser Gln Ser Xaa His Val Pro Xaa Thr
1               5

<210> SEQ ID NO 56
<211> LENGTH: 5
<212> TYPE: PRT
<213> ORGANISM: Artificial sequence
<220> FEATURE:
<223> OTHER INFORMATION: CDR1 of VH
<220> FEATURE:
<221> NAME/KEY: misc_feature
<222> LOCATION: (4)..(4)
<223> OTHER INFORMATION: Xaa can be Met or Ile

<400> SEQUENCE: 56

Gly Tyr Tyr Xaa His
1               5

<210> SEQ ID NO 57
<211> LENGTH: 17
<212> TYPE: PRT
<213> ORGANISM: Artificial sequence
<220> FEATURE:
<223> OTHER INFORMATION: CDR2 of VH
<220> FEATURE:
<221> NAME/KEY: misc_feature
<222> LOCATION: (6)..(6)
<223> OTHER INFORMATION: Xaa can be Ser or Asn
<220> FEATURE:
<221> NAME/KEY: misc_feature
<222> LOCATION: (8)..(8)
<223> OTHER INFORMATION: Xaa can be Asp or Glu
<220> FEATURE:
<221> NAME/KEY: misc_feature
<222> LOCATION: (9)..(9)
<223> OTHER INFORMATION: Xaa can be Thr or Ile
<220> FEATURE:
<221> NAME/KEY: misc_feature
<222> LOCATION: (13)..(13)
<223> OTHER INFORMATION: Xaa can be Gln or Pro
<220> FEATURE:
<221> NAME/KEY: misc_feature
<222> LOCATION: (16)..(16)
<223> OTHER INFORMATION: Xaa can be Lys or Arg

<400> SEQUENCE: 57

Leu Ile Ile Pro Tyr Xaa Gly Xaa Xaa Phe Tyr Asn Xaa Lys Phe Xaa
1               5                   10                  15

Gly

<210> SEQ ID NO 58
<211> LENGTH: 9
<212> TYPE: PRT
<213> ORGANISM: Artificial sequence
<220> FEATURE:
<223> OTHER INFORMATION: CDR3 of VH
<220> FEATURE:
<221> NAME/KEY: misc_feature
<222> LOCATION: (2)..(2)
<223> OTHER INFORMATION: Xaa can be Glu or Asp

<400> SEQUENCE: 58

Ala Xaa Val Ser Tyr Ala Met Asp Tyr
1               5
```

<210> SEQ ID NO 59
<211> LENGTH: 118
<212> TYPE: PRT
<213> ORGANISM: Artificial sequence
<220> FEATURE:
<223> OTHER INFORMATION: Heavy chain of h12H4-2

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Tyr Tyr
            20                  25                  30

Tyr Ile Gln Trp Val Arg Gln Ala Pro Gly Gln Arg Leu Glu Trp Met
        35                  40                  45

Gly Trp Ile Tyr Pro Gly Asn Gly Asn Ser Asn Ile Thr Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Phe Thr Thr Met Val Gly Asp Tyr Trp Gly Gln Gly Thr
            100                 105                 110

Thr Val Thr Val Ser Ser
        115

<210> SEQ ID NO 60
<211> LENGTH: 118
<212> TYPE: PRT
<213> ORGANISM: Artificial sequence
<220> FEATURE:
<223> OTHER INFORMATION: Heavy chain of h12H4-3

<400> SEQUENCE: 60

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Tyr Tyr
            20                  25                  30

Tyr Ile Gln Trp Val Arg Gln Ala Pro Gly Gln Gly Leu Glu Trp Met
        35                  40                  45

Gly Trp Ile Tyr Pro Gly Asn Gly Asn Ser Asn Ile Thr Glu Lys Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ile Phe Thr Thr Met Val Gly Asp Tyr Trp Gly Gln Gly Thr
            100                 105                 110

Thr Val Thr Val Ser Ser
        115

<210> SEQ ID NO 61
<211> LENGTH: 114
<212> TYPE: PRT
<213> ORGANISM: Artificial sequence
<220> FEATURE:
<223> OTHER INFORMATION: Light chain of h12H4-3

<400> SEQUENCE: 61

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
            100                 105                 110

Arg Thr

<210> SEQ ID NO 62
<211> LENGTH: 327
<212> TYPE: PRT
<213> ORGANISM: Artificial seaquence
<220> FEATURE:
<223> OTHER INFORMATION: hIgG4Pro

<400> SEQUENCE: 62

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp

```
                      245                 250                 255
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 63
<211> LENGTH: 330
<212> TYPE: PRT
<213> ORGANISM: Artificial seaquence
<220> FEATURE:
<223> OTHER INFORMATION: hIgG1

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 64
<211> LENGTH: 105
<212> TYPE: PRT
<213> ORGANISM: Artificial seaquence
<220> FEATURE:
<223> OTHER INFORMATION: hIgK

<400> SEQUENCE: 64

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105
```

MONOCLONAL ANTIBODY AGAINST NAV1.7

CROSS-REFERENCE TO RELATED APPLICATIONS

This application is a national stage application of International Application No. PCT/JP2019/021444, filed May 30, 2019, which is based upon and claims the benefit of priority to Japanese Patent Application No. 2018-104391, filed May 31, 2018. The entire contents of these applications are incorporated herein by reference.

TECHNICAL FIELD

The present invention relates to a novel monoclonal antibody against Nav1.7 or its antibody fragment. More particularly, the present invention relates to an antibody or its antibody fragment that specifically binds to Nav1.7. More particularly, the present invention relates to a monoclonal antibody or its antibody fragment that selectively inhibits Nav1.7 or its antibody fragment, or a pharmaceutical composition containing this one or a kit for detecting Nav1.7.

BACKGROUND ART

Nav1.7 is a voltage-gated sodium ion channel encoded by gene SCN9A and expressed primarily in peripheral nerves (Non-Patent Literature: 1). Nav1.7 comprises four domains A, B, C and D, each comprising six transmembrane protein helices (S1, S2, S3, S4, S5 and S6) and three extracellular hydrophilic loops E1, E2 and E3.

It is known that the inflammatory pain is reduced in a Nav1.7 knockout mouse (Non-Patent Literature: 2). It is confirmed that Nav1.7 inhibitor that is a low-molecular compound, is effective in erythromelalgia (Non-Patent Literature: 3), trigeminal neuralgia (Non-Patent literature: 4) and the like.

A monoclonal antibody against Nav1.7 that is effective for pain (algesic) and pruritus (itching) is reported in Patent Literatures: 1 to 7, etc. An antibody that binds to the E3 extracellular region of domain C is described in Patent Literatures: 1 to 3.

CITATION LIST

Patent Literature

[Patent Literature: 1] WO2011/051350
[Patent Literature: 2] U.S. Pat. No. 8,734,798
[Patent Literature: 3] U.S. Pat. No. 8,986,954
[Patent Literature: 4] U.S. Pat. No. 9,266,953
[Patent Literature: 5] WO2014/159595
[Patent Literature: 6] WO2015/032916
[Patent Literature: 7] WO2015/035173

Non-Patent Literature

[Non-Patent Literature: 1] PNAS(1997)94:1527-1532
[Non-patent Document: 2] PNAS(2004)101:12706-12711
[Non-patent Document: 3] Pain(2012)153(1):80-85
[Non-patent Document: 4] THE LANCET NEUROLOGY (2017)16(4):291-300

SUMMARY OF INVENTION

Problem to be Solved by the Invention

An object of the present invention is to provide a novel monoclonal antibody against Nav1.7 or its antibody fragment that can be used as therapeutic agent for pain, pruritus and the like.

Solution to Problem

The present inventors have conducted diligent studies and found a monoclonal antibody that specifically binds to the E3 extracellular region of domain C of Nav1.7 and selectively inhibits Nav1.7. We also found that the monoclonal antibody of the present invention has analgesic or pruritus inhibitory effects.

Specifically, this present invention relates to:

(1-1)

A monoclonal antibody or its antibody fragment that binds to Nav1.7, having
a1) a heavy chain variable region
 including a CDR1 having the amino acid sequence of SEQ ID NO: 27, a CDR2 having the amino acid sequence of SEQ ID NO: 28 and a CDR3 having the amino acid sequence of SEQ ID NO: 29, wherein one or two amino acids may be deleted, substituted, inserted and/or added, and
a light chain variable region
 including a CDR1 having the amino acid sequence of SEQ ID NO: 34, a CDR2 having the amino acid sequence of SEQ ID NO: 35 and a CDR3 having the amino acid sequence of SEQ ID NO: 50, wherein one or two amino acids may be deleted, substituted, inserted and/or added;
 (i.e., heavy and light chain variable regions including CDRs of 12H4, h12H4, h12H4-2 and h12H4-3 according to the example or variants thereof)
a heavy chain variable region including
b1-1) a CDR1 having the amino acid sequence of SEQ ID NO: 3, a CDR2 having the amino acid sequence of SEQ ID NO: 4 and a CDR3 having the amino acid sequence of SEQ ID NO: 5, wherein one or two amino acids may be deleted, substituted, inserted and/or added,
b1-2) a CDR1 having the amino acid sequence of SEQ TD NO: 15, a CDR2 having the amino acid sequence of SEQ ID NO: 16 and a CDR3 having the amino acid sequence of SEQ ID NO: 17, wherein one or two amino acids may be deleted, substituted, inserted and/or added,
b1-3) a CDR1 having the amino acid sequence of SEQ ID NO: 15, a CDR2 having the amino acid sequence of SEQ ID NO: 24 and a CDR3 having the amino acid sequence of SEQ ID NO: 25, wherein one or two amino acids may be deleted, substituted, inserted and/or added, or
b1-4) a CDR1 having the amino acid sequence of SEQ ID NO: 21, a CDR2 having the amino acid sequence of SEQ ID NO: 22 and a CDR3 having the amino acid sequence of SEQ ID NO: 17, wherein one or two amino acids may be deleted, substituted, inserted and/or added, and
a light chain variable region
 including a CDR1 having the amino acid sequence of SEQ ID NO: 34, a CDR2 having the amino acid sequence of SEQ ID NO: 35 and a CDR3 having the amino acid sequence of SEQ ID NO: 36, wherein one or two amino acids may be deleted, substituted, inserted and/or added;

(i.e., heavy and light chain variable regions including CDRs of 3B2, 3B2/15C8, 15C8, 29G3, or 28B5/15C8 according to the example or variants thereof)

c1) a heavy chain variable region
  including a CDR1 having the amino acid sequence of SEQ ID NO: 7, a CDR2 having the amino acid sequence of SEQ ID NO: 8 and a CDR3 having the amino acid sequence of SEQ ID NO: 9, wherein one or two amino acids may be deleted, substituted, inserted and/or added, and
  a light chain variable region
  including a CDR1 having the amino acid sequence of SEQ ID NO: 38, a CDR2 having the amino acid sequence of SEQ ID NO: 39 and a CDR3 having the amino acid sequence of SEQ ID NO: 40, wherein one or two amino acids may be deleted, substituted, inserted and/or added;

(i.e., heavy and light chain variable regions including CDRs of 5E12 according to the example or variants thereof)

d1) a heavy chain variable region
  including a CDR1 having the amino acid sequence of SEQ ID NO: 11, a CDR2 having the amino acid sequence of SEQ ID NO: 12 and a CDR3 having the amino acid sequence of SEQ ID NO: 13, wherein one or two amino acids may be deleted, substituted, inserted and/or added, and
  a light chain variable region
  including a CDR1 having the amino acid sequence of SEQ ID NO: 38, a CDR2 having the amino acid sequence of SEQ ID NO: 42 and a CDR3 having the amino acid sequence of SEQ ID NO: 40, wherein one or two amino acids may be deleted, substituted, inserted and/or added;

(i.e., heavy and light chain variable regions including CDRs of 7B9 according to the example, or variants thereof)

e1) a heavy chain variable region
  including a CDR1 having the amino acid sequence of SEQ ID NO: 15, a CDR2 having the amino acid sequence of SEQ ID NO: 19 and a CDR3 having the amino acid sequence of SEQ ID NO: 17, wherein one or two amino acids may be deleted, substituted, inserted and/or added, and
  a light chain variable region
  including a CDR1 having the amino acid sequence of SEQ ID NO: 34, a CDR2 having the amino acid sequence of SEQ ID NO: 45 and a CDR3 having the amino acid sequence of SEQ ID NO: 36, wherein one or two amino acids may be deleted, substituted, inserted and/or added;

(i.e., heavy and light chain variable regions including CDRs of 15H6 according to the example or variants thereof)

a heavy chain variable region including f1-1) a CDR1 having the amino acid sequence of SEQ ID NO: 21, a CDR2 having the amino acid sequence of SEQ ID NO: 22 and a CDR3 having the amino acid sequence of SEQ ID NO: 17, wherein one or two amino acids may be deleted, substituted, inserted and/or added, or f1-2) a CDR1 having the amino acid sequence of SEQ ID NO: 3, a CDR2 having the amino acid sequence of SEQ ID NO: 4 and a CDR3 having the amino acid sequence of SEQ ID NO: 5, wherein one or two amino acids may be deleted, substituted, inserted and/or added, and a light chain variable region
  including a CDR1 having the amino acid sequence of SEQ ID NO: 34, a CDR2 having the amino acid sequence of SEQ ID NO: 35 and a CDR3 having the amino acid sequence of SEQ ID NO: 47, wherein one or two amino acids may be deleted, substituted, inserted and/or added;

(i.e., heavy and light chain variable regions including CDRs of 28B5 or 3B2/28B5 according to the example or variants thereof)

g1) a heavy chain variable region
  including a CDR1 having the amino acid sequence of SEQ ID NO: 31, a CDR2 having the amino acid sequence of SEQ ID NO: 32 and a CDR3 having the amino acid sequence of SEQ ID NO: 29, wherein one or two amino acids may be deleted, substituted, inserted and/or added, and
  a light chain variable region
  including a CDR1 having the amino acid sequence of SEQ ID NO: 34, a CDR2 having the amino acid sequence of SEQ ID NO: 35 and a CDR3 having the amino acid sequence of SEQ ID NO: 50, wherein one or two amino acids may be deleted, substituted, inserted and/or added;

(i.e., heavy and light chain variable regions including CDRs of 22D3 according to the example or variants thereof)

h1) a heavy chain variable region
  including a CDR1 having the amino acid sequence of SEQ ID NO: 56: G-Y-Y-Xaa4-H (wherein Xaa4 is M or I), a CDR2 having the amino acid sequence of SEQ ID NO: 57: L-I-I-P-Y-Xaa5-G-Xaa6-Xaa7-F-Y-N-Xaa8-K-F-Xaa9-G (wherein Xaa5 is S or N, Xaa6 is D or E, Xaa7 is T or I, Xaa8 is Q or P, and Xaa9 is K or R) and a CDR3 having the amino acid sequence of SEQ ID NO: 58: A-Xaa10-V-S-Y-A-M-D-Y (wherein Xaa10 is E or D), wherein one or two amino acids may be deleted, substituted, inserted and/or added, and
  a light chain variable region
  including a CDR1 having the amino acid sequence of SEQ ID NO: 34, a CDR2 having the amino acid sequence of SEQ ID NO: 54: K-V-S-N-R-Xaa1-S (wherein Xaa1 is F or I) and a CDR3 having the amino acid sequence of SEQ ID NO: 55: S-Q-S-Xaa2-H-V-P-Xaa3-T (wherein Xaa2 is T or 1, and Xaa3 is F or W), wherein one or two amino acids may be deleted, substituted, inserted and/or added.

(i.e., heavy and light chain variable regions including CDRs having consensus sequences of a plurality of antibodies according to Example 3, or variants thereof)

(1-2) The antibody or its antibody fragment according to (1-1), having
  a heavy chain variable region including
    a CDR1 having the amino acid sequence of SEQ ID NO: 27, wherein one or two amino acids may be deleted, substituted, inserted and/or added at any position other than position 10; a CDR2 having the amino acid sequence of SEQ ID NO: 28, wherein one or two amino acids may be deleted, substituted, inserted and/or added, and a CDR3 having the amino acid sequence of SEQ ID NO: 29, wherein one or two amino acids may be deleted, substituted, inserted and/or added at any position other than position 2 and 6, and
  a light chain variable region
  including a CDR1 having the amino acid sequence of SEQ ID NO: 34, wherein one or two amino acids may be deleted, substituted, inserted and/or added, a CDR2 having the amino acid sequence of SEQ ID NO: 35, wherein one or two amino acids may be deleted, substituted, inserted and/or added, and a CDR3 having the amino acid sequence of SEQ ID NO: 50, wherein one or two amino acids may be deleted, substituted, inserted and/or added at any position other than position 5.

(i.e., heavy and light chain variable regions including CDRs in which critical sequences in 12H4 are essential according to Example 6 or variants thereof)

(2) The antibody or its antibody fragment according to (1-1) or (1-2), having a1) a heavy chain variable region
　including a CDR1 having the amino acid sequence of SEQ ID NO: 27, a CDR2 having the amino acid sequence of SEQ ID NO: 28 and a CDR3 having the amino acid sequence of SEQ ID NO: 29, and
　a light chain variable region
　including a CDR1 having the amino acid sequence of SEQ ID NO: 34, a CDR2 having the amino acid sequence of SEQ ID NO: 35 and a CDR3 having the amino acid sequence of SEQ ID NO: 50;

(i.e., heavy and light chain variable regions including CDRs of 12H4, h12H4, h12H4-2 and h12H4-3 according to the example)

a heavy chain variable region including
b1-1) a CDR1 having the amino acid sequence of SEQ ID NO: 3, a CDR2 having the amino acid sequence of SEQ ID NO: 4 and a CDR3 having the amino acid sequence of SEQ ID NO: 5,
b1-2) a CDR1 having the amino acid sequence of SEQ ID NO: 15, a CDR2 having the amino acid sequence of SEQ ID NO: 16 and a CDR3 having the amino acid sequence of SEQ ID NO: 17,
b1-3) a CDR1 having the amino acid sequence of SEQ ID NO: 15, a CDR2 having the amino acid sequence of SEQ ID NO: 24 and a CDR3 having the amino acid sequence of SEQ ID NO: 25, or
b1-4) a CDR1 having the amino acid sequence of SEQ ID NO: 21, a CDR2 having the amino acid sequence of SEQ ID NO: 22 and a CDR3 having the amino acid sequence of SEQ ID NO: 17, and
　a light chain variable region
　including a CDR1 having the amino acid sequence of SEQ ID NO: 34, a CDR2 having the amino acid sequence of SEQ ID NO: 35 and a CDR3 having the amino acid sequence of SEQ ID NO: 36;

(i.e., heavy and light chain variable regions including CDRs of 3B2, 3B2/15C8, 15C8, 29G3 or 28B5/15C8 according to the example)

c1) a heavy chain variable region
　including a CDR1 having the amino acid sequence of SEQ ID NO: 7, a CDR2 having the amino acid sequence of SEQ ID NO: 8 and a CDR3 having the amino acid sequence of SEQ ID NO: 9, and
　a light chain variable region
　including a CDR1 having the amino acid sequence of SEQ ID NO: 38, a CDR2 having the amino acid sequence of SEQ ID NO: 39 and a CDR3 having the amino acid sequence of SEQ ID NO: 40;

(i.e., heavy and light chain variable regions including CDRs of 5E12 according to the example);

d1) a heavy chain variable region
　including a CDR1 having the amino acid sequence of SEQ ID NO: 11, a CDR2 having the amino acid sequence of SEQ ID NO: 12 and a CDR3 having the amino acid sequence of SEQ ID NO: 13, and
　a light chain variable region
　including a CDR1 having the amino acid sequence of SEQ ID NO: 38, a CDR2 having the amino acid sequence of SEQ ID NO: 42 and a CDR3 having the amino acid sequence of SEQ ID NO: 40;

(i.e., heavy and light chain variable regions including CDRs of 7B9 according to the example)

e1) a heavy chain variable region
　including a CDR1 having the amino acid sequence of SEQ ID NO: 15, a CDR2 having the amino acid sequence of SEQ ID NO: 19 and a CDR3 having the amino acid sequence of SEQ ID NO: 17, and
　a light chain variable region
　including a CDR1 having the amino acid sequence of SEQ ID NO: 34, a CDR2 having the amino acid sequence of SEQ ID NO: 45 and a CDR3 having the amino acid sequence of SEQ ID NO: 36;

(i.e., heavy and light chain variable regions including CDRs of 15H6 according to the example); a heavy chain variable region including f1-1) a CDR1 having the amino acid sequence of SEQ ID NO: 21, a CDR2 having the amino acid sequence of SEQ ID NO: 22 and a CDR3 having the amino acid sequence of SEQ ID NO: 17, or
f1-2) a CDR1 having the amino acid sequence of SEQ ID NO: 3, a CDR2 having the amino acid sequence of SEQ ID NO: 4 and a CDR3 having the amino acid sequence of SEQ ID NO: 5, and
　a light chain variable region
　including a CDR1 having the amino acid sequence of SEQ ID NO: 34, a CDR2 having the amino acid sequence of SEQ ID NO: 35 and a CDR3 having the amino acid sequence of SEQ ID NO: 47;

(i.e., heavy and light chain variable regions including CDRs of 28B5 or 3B2/28B5 according to the example);

g1) a heavy chain variable region
　including a CDR1 having the amino acid sequence of SEQ ID NO: 31, a CDR2 having the amino acid sequence of SEQ ID NO: 32 and a CDR3 having the amino acid sequence of SEQ ID NO: 29, and
　a light chain variable region
　including a CDR1 having the amino acid sequence of SEQ ID NO: 34, a CDR2 having the amino acid sequence of SEQ ID NO: 35 and a CDR3 having the amino acid sequence of SEQ ID NO: 50; or (i.e., heavy and light chain variable regions including CDRs of 22D3 according to the example);

h1) a heavy chain variable region
　including a CDR1 having the amino acid sequence of SEQ ID NO: 56, a CDR2 having the amino acid sequence of SEQ ID NO: 57 and a CDR3 having the amino acid sequence of SEQ ID NO: 58, and
　a light chain variable region
　including a CDR1 having the amino acid sequence of SEQ ID NO: 34, a CDR2 having the amino acid sequence of SEQ ID NO: 54 and a CDR3 having the amino acid sequence of SEQ ID NO: 55.

(i.e., heavy and light chain variable regions including CDRs having consensus sequences of a plural of antibodies according to Example 3)

(3) The antibody or its antibody fragment according to (1-1) or (1-2), having a2) a heavy chain variable region
　having an amino acid sequence of SEQ ID NO: 52, 59 or 60 or an amino acid sequence at least 95% identical to the amino acid sequence of SEQ ID NO: 52, 59 or 60, and a light chain variable region
having an amino acid sequence of SEQ ID NO: 53 or 61 or an amino acid sequence at least 95% identical to the amino acid sequence of SEQ ID NO: 53 or 61;
b2) a heavy chain variable region
having an amino acid sequence of SEQ ID NO: 26 or an amino acid sequence at least 95% identical to the amino acid sequence of SEQ ID NO: 26, and
a light chain variable region
having an amino acid sequence of SEQ ID NO: 49 or an amino acid sequence at least 95% identical to the amino acid sequence of SEQ ID NO: 49;
c2) a heavy chain variable region
having an amino acid sequence of SEQ ID NO: 23 or an amino acid sequence at least 95% identical to the amino acid sequence of SEQ ID NO: 23, and
a light chain variable region
having an amino acid sequence of SEQ ID NO: 48 or an amino acid sequence at least 95% identical to the amino acid sequence of SEQ ID NO: 48;
d2) a heavy chain variable region
having an amino acid sequence of SEQ ID NO: 2 or an amino acid sequence at least 95% identical to the amino acid sequence of SEQ ID NO: 2, and
a light chain variable region
having an amino acid sequence of SEQ ID NO: 33 or an amino acid sequence at least 95% identical to the amino acid sequence of SEQ ID NO: 33;
c2) a heavy chain variable region
having an amino acid sequence of SEQ ID NO: 6 or an amino acid sequence at least 95% identical to the amino acid sequence of SEQ ID NO: 6, and
a light chain variable region
having an amino acid sequence of SEQ ID NO: 37 or an amino acid sequence at least 95% identical to the amino acid sequence of SEQ ID NO: 37;
f2) a heavy chain variable region
having an amino acid sequence of SEQ ID NO: 10 or an amino acid sequence at least 95% identical to the amino acid sequence of SEQ ID NO: 10, and
a light chain variable region
having an amino acid sequence of SEQ ID NO: 41 or an amino acid sequence at least 95% identical to the amino acid sequence of SEQ ID NO: 41;
g2) a heavy chain variable region
having an amino acid sequence of SEQ ID NO: 14 or an amino acid sequence at least 95% identical to the amino acid sequence of SEQ ID NO: 14, and
a light chain variable region
having an amino acid sequence of SEQ ID NO: 43 or an amino acid sequence at least 95% identical to the amino acid sequence of SEQ ID NO: 43;
h2) a heavy chain variable region
having an amino acid sequence of SEQ ID NO: 18 or an amino acid sequence at least 95% identical to the amino acid sequence of SEQ ID NO: 18, and
a light chain variable region
having an amino acid sequence of SEQ ID NO: 44 or an amino acid sequence at least 95% identical to the amino acid sequence of SEQ ID NO: 44;
i2) a heavy chain variable region
having an amino acid sequence of SEQ ID NO: 20 or an amino acid sequence at least 95% identical to the amino acid sequence of SEQ ID NO: 20, and
a light chain variable region
having an amino acid sequence of SEQ ID NO: 46 or an amino acid sequence at least 95% identical to the amino acid sequence of SEQ ID NO: 46;
j2) a heavy chain variable region
having an amino acid sequence of SEQ ID NO: 30 or an amino acid sequence at least 95% identical to the amino acid sequence of SEQ ID NO: 30, and
a light chain variable region
having an amino acid sequence of SEQ ID NO: 51 or an amino acid sequence at least 95% identical to the amino acid sequence of SEQ ID NO: 51;
k2) a heavy chain variable region
having an amino acid sequence of SEQ ID NO: 2 or an amino acid sequence at least 95% identical to the amino acid sequence of SEQ ID NO: 2, and
a light chain variable region
having an amino acid sequence of SEQ ID NO: 46 or an amino acid sequence at least 95% identical to the amino acid sequence of SEQ ID NO: 46;
l2) a heavy chain variable region
having an amino acid sequence of SEQ ID NO: 2 or an amino acid sequence at least 95% identical to the amino acid sequence of SEQ ID NO: 2, and
a light chain variable region
having an amino acid sequence of SEQ ID NO: 43 or an amino acid sequence at least 95% identical to the amino acid sequence of SEQ ID NO: 43; or
m2) a heavy chain variable region
having an amino acid sequence of SEQ ID NO: 20 or an amino acid sequence at least 95% identical to the amino acid sequence of SEQ ID NO: 20, and
a light chain variable region
having an amino acid sequence of SEQ ID NO: 43 or an amino acid sequence at least 95% identical to the amino acid sequence of SEQ ID NO: 43.

Concrete examples of antibodies are listed in Table 1 in Example.

(4) The antibody or its antibody fragment according to (3) having
a2-1) a heavy chain variable region having an amino acid sequence of SEQ ID NO: 52, and a light chain variable region having an amino acid sequence of SEQ ID NO: 53;
a2-2) a heavy chain variable region having an amino acid sequence of SEQ ID NO: 59, and a light chain variable region having an amino acid sequence of SEQ ID NO: 53; or
a2-3) a heavy chain variable region having an amino acid sequence of SEQ ID NO: 60, and a light chain variable region having an amino acid sequence of SEQ ID NO: 61.

(5) The antibody or its antibody fragment according to any of (1) to (4), further having
a heavy chain constant region having an amino acid sequence of SEQ ID NO: 62 or 63, and
a light chain constant region having an amino acid sequence of SEQ ID NO: 64.

Concrete examples of antibodies in (4) and (5) are listed in Table 2 in Example.

(6) A pharmaceutical composition comprising the antibody or its antibody fragment according to any of (1-1), (1-2) and (2)-(5).

(7) The pharmaceutical composition according to (6) for treating or preventing pain and/or pruritus.

(8) A polynucleotide encoding a heavy chain variable region of antibody according to (3) or (4), wherein the polynucleotide optionally encodes a heavy chain constant region of antibody according to (5).

(9) A polynucleotide encoding a light chain variable region of antibody according to (3) or (4), wherein the polynucleotide optionally encodes a light chain constant region of antibody according to (5).
(10) An expression vector comprising the polynucleotide according to (8) or (9).
(11) A polynucleotide encoding the antibody or its antibody fragment according to any of (1-1), (1-2), and (2)-(5).
(12) The antibody of its antibody fragment according to any of (1-1), (1-2), and (2)-(5), wherein the fragment is Fab, Fab', F(ab')$_2$, scFv, dsFv or Diabody.
(13) A method for the preventing or treating a Nav1.7 related disease comprising administration of the monoclonal antibody or its antibody fragment, according to any of (1-1), (1-2), and (2)-(5).
(14) The monoclonal antibody or its antibody fragment according to any of (1-1), (1-2) and (2)-(5) for manufacturing treatment or prevention agent of a Nav1.7 related disease.
(15) The monoclonal antibody or its antibody fragment according to any of (1-1), (1-2) and (2)-(5) for treating or preventing a Nav1.7 related disease.
(16) The method according to (13), or the antibody or its antibody fragment according to (14) or (15), wherein a Nav1.7-related disease is pain and/or pruritus.
(17) A kit for detecting Nav1.7 comprising the monoclonal antibody or its antibody fragment according to any of (1-1), (1-2) and (2)-(5).

Effect of the Invention

Since a monoclonal antibody or its antibody fragment of the present invention specifically binds to Nav1.7, it may be used to detect Nav1.7 in biological samples. In addition, since the monoclonal antibody or its antibody fragment of the present invention has the activity to selectively inhibit Nav1.7, a pharmaceutical composition comprising it is great useful for medicine, particularly for treatment or prevention of a Nav1.7 related disease.

BRIEF DESCRIPTION OF THE DRAWINGS

FIG. 1 Kabat numbering and alignment results of the heavy chain of 15C8 (SEQ ID NO: 14), 15H6 (SEQ ID NO: 18), 28B5 (SEQ ID NO: 20), and 29G3 (SEQ ID NO: 23)
FIG. 2 Kabat numbering and alignment results of the light chain of 15C8 (SEQ ID NO: 43), the light chain of 15H6 (SEQ ID NO: 44), 28B5 (SEQ ID NO: 46) and 29G3 (SEQ ID NO: 48)
FIG. 3 Kabat numbering of the heavy chain of h12H4 (SEQ ID NO:52, FIG. 3A) and the light chain of h12H4 (SEQ ID NO:53, FIG. 3B)
FIG. 4 Drug efficacy assessment by local intraplantar administration to sciatic nerve part ligation models
FIG. 5 Drug efficacy assessment by intravenous administration to sciatic nerve part ligation models

MODE FOR CARRYING OUT THE INVENTION

Figure 4:
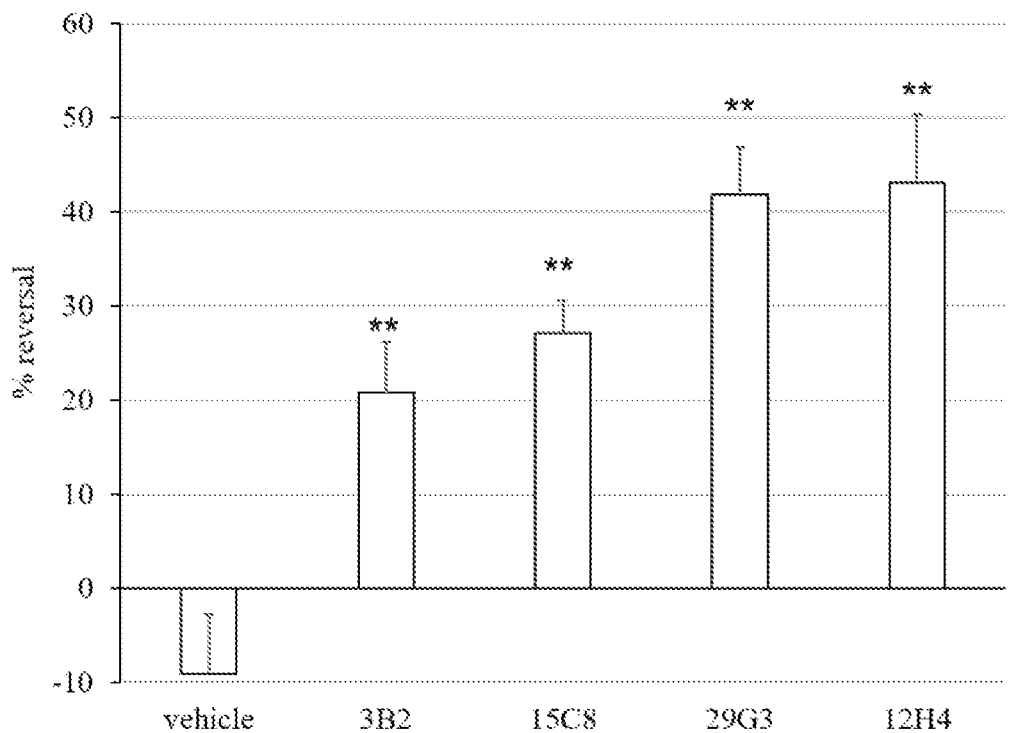

Terms in the present specification refer to commonly used meanings in the art, unless otherwise mentioned.
In the present invention, techniques known in the art are available for producing antibodies. Examples include the methods described in Immunochemistry in Practice (Blackwell Scientific Publications).
Genetic engineering techniques known in the art are also available. Examples include the methods described in Molecular Cloning, A Laboratory Manual, Fourth Edition, Cold Spring Harbor Laboratory Press (2012), Current Protocols Essential Laboratory Techniques, Current Protocols (2012).

Human Nav1.7 is protein (UniProtKB/Swiss-Prot: Q15858) consisting of amino acids encoded by gene SCN9A.

The monoclonal antibody or its antibody fragment in the present invention is the monoclonal antibody or its antibody fragment having the CDRs or the heavy/light chain variable regions described in the present specification. The antibody or its antibody fragment may be derived from any class (e.g., IgG, IgE, IgM, IgD or IgA) or subclass of immunoglobulin molecules and may be obtained from any species including mouse, rat, shark, rabbit, pig, hamster, camel, llama, goat and human. The preferable antibody or its antibody fragment is the humanized monoclonal antibody or its antibody fragment.

In the invention, "an antibody fragment of a monoclonal antibody" means a portion of a monoclonal antibody, wherein the fragment specifically binds to Nav1.7 and selectively inhibits Nav1.7 as well as said monoclonal antibody.

Specific examples include Fab (fragment of antigen binding), Fab', F(ab')$_2$, single-chain antibody (single chain Fv; hereinafter referred to as scFv), disulfide stabilized antibody (disulfide stabilized Fv; hereinafter referred to as dsFv), dimerized V-region fragments (hereinafter referred to as Diabody) and peptides containing CDRs which specifically bind to human Nav1.7 (Expert Opinion on Therapeutic Patents, Vol. 6, No. 5, pp. 441-456, 1996).

Fab is an antibody fragment having about 50,000 in molecular weight with antigen-binding activity, consisting of about a half of the N-terminal region of H-chain and the whole L-chain, obtained by degrading with enzyme papain the peptide part at the top of the two disulfide bonds (S—S bonds) that cross-link two H-chains in hinge region of IgG. Fab used in the present invention may be obtained by treating with papain the monoclonal antibody of the present invention. Alternatively, Fab may be produced by inserting the DNA encoding Fab of the monoclonal antibody of the present invention into an expression vector and by transducing the vector into a cell to express.

Fab' is an antibody fragment having about 50,000 in molecular weight and antigen-binding activity with the cleaved S—S bonds between the hinges of the F(ab')$_2$. Fab' used in the present invention may be obtained by treating the monoclonal antibody F(ab')$_2$ in the present invention with the reductant dithiothreitol. The Fab' may also be produced by inserting the DNA encoding the Fab' of the monoclonal antibody in the present invention into an expression vector for cells and transducing the vector into E. coli, yeasts or animal cells to express.

F(ab')$_2$ is an antibody fragment having about 100,000 in molecular weight with antigen-binding activity, formed by binding two Fab' regions in a hinge part obtained by degrading with enzyme pepsin the lower part of the two S—S bonds in the hinge region of IgG. The F(ab')$_2$ used in the present invention may be obtained by treating the monoclonal antibody of the present invention with pepsin. Alternatively, the F(ab')$_2$ used in the present invention may also be produced by inserting the DNA encoding the F(ab')$_2$ of the monoclonal antibody into an expression vector for cells and transducing the vector into E. coli, yeasts or animal cells to express.

ScFv is a VH-P-VL or VL-P-VH polypeptide in which one VH chain and one VL chain are connected using an appropriate peptide linker (hereinafter denoted by P) and it is an antibody fragment having an antigen activity. The VH and the VL contained in the scFv used in the present invention may be derived from those of the monoclonal antibody of the present invention. The ScFv used in the present invention may be produced by constructing a scFV expression vector by using cDNA encoding the VH and the VL monoclonal antibody of the present invention, and by transducing the vector into E. coli, yeasts or animal cells to express.

dsFv refers to one obtained by binding polypeptides in which each one amino acid residue in a VH and a VL is substituted with a cysteine residue via S—S bond. The amino acid residue substituted into cysteine residue may be selected based on tertiary structure prediction of the antibody according to the method indicated by Reiter et al. (Protein Engineering, 7, 697 (1994)). The VH or the VL contained in the dsFv in the present invention may be derived from the monoclonal antibody of the present invention. The dsFv used in the present invention may be produced by inserting to proper expression vector by using cDNA encoding the VH and the VL monoclonal antibody in the present invention to construct the dsFV expression vector, and by transducing the vector into E. coli, yeasts or animal cells to express.

Diabody is an antibody fragment with the scFv having the same or different antigen binding specificity forming a dimer, and an antibody fragment having divalent antigen binding activity for the same antigen or two kinds of antigen-binding activities specific for the different antigen. For example, divalent Diabody that specifically reacts with the monoclonal antibody of the present invention may be produced by constructing DNA encoding scFV with a peptide linker of 3 to 10 resides using cDNA encoding VH and VL of a monoclonal antibody of the present invention, inserting the DNA into a cellular expression vector for cells and transducing the vector into E. coli, yeasts or animal cells to express Diabody.

Peptide containing CDR includes at least one or more regions of CDR in VH or VL. Plural CDRs may be linked directly or via an appropriate peptide linker. The peptide containing CDR in the present invention may be produced by constructing a DNA encoding the CDR using a cDNA encoding a VH and a VL of a monoclonal antibody in the present invention, inserting the DNA into an expression vector for animal cell and transducing the vector into E. coli, yeasts or animal cells to express. The peptide containing CDR may also be produced by the chemical synthetic methods such as Fmoc method (fluorenyl methyloxycarbonyl method) or tBoc method (t-butyloxycarbonyl method).

The monoclonal antibody or its antibody fragment of the present invention is characterized by specific binding to Nav1.7. An example of procedures for measuring the specific binding ability to Nav1.7 is shown as follows.

Specific bonds may be characterized by an equilibrium dissociation constant of at least about $1 \times 10^{-6}$ M or less (e.g., smaller KD represents tighter bonds). Methods for determining whether two molecules bind specifically are well known in the art, and they include the competitive ELISA method described in Example 5 and the surface plasmon resonance. However, an isolated antibody that specifically binds Nav1.7 may exhibit a cross-reactivity to other antigens, such as Nav1.7 molecules derived from other species. Nevertheless, a multi-specific antibody that binds to hNav1.7 and one or more additional antigens, or a bispecific antibody that binds to two distinct regions of hNav1.7 (e.g., EC loop 3-1 and EC loop 3-3), is considered to be an antibody that "specifically binds" to hNav1.7.

The monoclonal antibody or its antibody fragment of the present invention is characterized by inhibiting Nav1.7. Show an example of measurement procedure of the inhibitory ability of Nav1.7 below.

The DNA encoding Nav1.7 is cloned into pcDNA3.1 (Invitrogen). The expression vector is transfected into FreeStyle 293 cells (Thermo Fisher Scientific) to construct Nav1.7 stable expression cells. Nav1.7 specific inhibition of the antibody is assessed by performing manual patch clamping using this cell, according to the methods described below. Poly-L-lysine coated glass pieces are arranged in 35 mm dishes. Nav1.7 stable expression cells suspended in 10% FBS-containing DMEM (SIGMA) are seeded on the dishes (4×10 4 cells/dish). On the day after seeding, the glass pieces are transferred to a measuring chamber to form whole cells. The antibody is treated with −70 mV fixation and 10 msec square wave at 0.1 Hz. Measurement is carried out before and after the antibody treatment (>2 min action taken).

The monoclonal antibody of the present invention may be produced by using the CDRs or the heavy and light chain variable regions described in the present specification, according to the routine methods in the art.

The monoclonal antibody of the present invention further includes a humanized monoclonal antibody. A humanized antibody has reduced antigenicity in the human body, so it's useful for administration into humans for the purpose of therapy and the like. A humanized monoclonal antibody is obtained by transplanting a complementarity determining region (CDR) of antibody of a mammal other than human such as mouse, into the framework region (FR) of human antibody. Therefore, the FR region derives from human antibody. Suitable FRs may be selected by referring to literatures of Kabat E A. et al. FR can be selected in such a manner that CDR can form appropriate antigen-binding site. If necessary, the amino acids of the FRs of the variable regions may be substituted so that the CDRs of the reconstituted humanized antibody can form appropriate antigen-binding site (Sato, K. et al., Cancer Res. Vol. 53, p. 851, 1993). The proportion of substituted amino acids in the FR is 0 to 15% of all FR region, preferably 0 to 5%, of all FR region.

Furthermore, as a humanized antibody of the present invention, constant region of the human antibody is available. As a preferred human antibody constant region, Cγ can be recited for the heavy chain, and for example, Cγ1, Cγ2, Cγ3 and Cγ4 can be used. Cκ and Cλ, can be recited for the light chain. Further, human antibody C region may be modified to improve its stability of antibody or its productivity. In humanization, available human antibody may be any isotype such as IgG, IgM, IgA, IgE and IgD. In the present invention, IgG is preferable and IgG1 or IgG4 is more preferable.

The humanized monoclonal antibody of the present invention may or may not have lysine added to the C-terminus of the heavy chain constant regions. Preferably, it has a light chain constant region of the amino acid sequence of SEQ ID NO: 64 and a heavy chain constant region of the amino acid sequence of SEQ ID NO: 62 or 63 and may or may not have a lysine added to the C-terminus of SEQ ID NO: 62 or 63.

The humanized monoclonal antibody may be produced by conventional manufacture methods (see, e.g., Example 4 below, the publication WO95/14041 and the publication WO96/02576). Specifically, a DNA sequence encoding a variable region designed to link the CDR of a murine antibody to the FR of a human antibody is synthesized by PCR method from a number of oligonucleotides prepared to have part overlapping the ends (see WO98/13388 publication). The obtained DNA is ligated with DNA encoding the constant region of a human antibody and then inserted into an expression vector. Alternatively, the DNA encoding the variable region of the antibody may be inserted into an expression vector comprising the DNA of the constant region of the antibody. For manufacture of antibodies in the present invention, antibody genes are inserted into expression vectors to express under the control of expression control regions, e.g., enhancers/promoters. Then, the expression vector can transform the host cells to express the antibody.

Host cells of the above transformants include vertebrate cells such as COS cells or CHO cells, prokaryotes and yeasts. Transformants can be cultured by the methods known for the skilled person. By this culture, the monoclonal antibody of the present invention is produced in or outside the transformants. Medium for the culture can appropriately be selected from conventional mediums depending on the host cell. In the case of COS cells, RPMI-1640 medium and Dulbecco's Modified Eagle's Minimal Essential Medium (DMEM) are available and if necessary, the scrum ingredients likewise Fetal Bovine Serum (FBS) can be added. The temperature for cultivating the transformants is not restricted, as far as not lowering the ability to produce proteins in the cell seriously. Preferably temperatures of 32 to 42° C. is recited. Most preferably, temperature of 37° C. is recited. As necessary, cultivating can be performed in the atmosphere containing carbon dioxide of 1 to 10% (v/v).

Fractions containing the monoclonal antibody of the present invention which are produced in or outside the transformants by the methods previously described, can be separated and purified by the heretofore known separation methods. These methods are based on physical or chemical property of the target protein. Concretely, examples include treatment with conventional protein precipitant, ultrafiltration, molecular sieve chromatography (gel filtration), adsorption chromatography, ion-exchange chromatography, affinity chromatography, various chromatography such as high-performance liquid chromatography (HPLC), dialysis, and combinations thereof. The methods make it possible to easily manufacture the monoclonal antibody in the present invention with high yields and purities.

The monoclonal antibody or its active fragment of the present invention may further be modulated by various molecules such as polyethylene glycols (PEGs), radioactive materials, toxins, and the like. Methods known in this art are available for antibody modification.

The monoclonal antibody of the present invention may also be fused to the other protein at their N- or C-terminal (Clinical Cancer Research, 2004, 10, 1274-1281). The skilled person can approximately select the fused protein.

The pharmaceutical composition containing the monoclonal antibody or its antibody fragment of the present invention (a pharmaceutical composition of the present invention) can be administered systemically or topically by orally or parentally. For parenteral administration, for example, intravenous injection such as drip infusion, intramuscular injection, intraperitoneal injection, subcutaneous injection, intranasal administration, inhalation and the like can be selected.

The pharmaceutical composition in the present invention is highly useful as a medicine for treatment and/or prevention of Nav1.7 related diseases.

Nav1.7 related diseases include pain, pruritus, neurogenic inflammations, cough, and the like.

"Pain" includes acute pains, chronic pains, neuropathic pains, inflammatory pain, arthritis, osteoarthritis, migraine, cluster headaches, trigeminal neuralgia, herpetic neuralgia, generalized neuralgia, neurodegenerative diseases, movement disorders, neuroendocrine disorders, ataxia, sepsis, visceral pain, acute gout, post-herpetic neuralgia, diabetic neuropathy, sciatica, back pain, head or neck pain, severe pain or intractable pain, sudden pain, pain after surgery, erythromelalgia genetic, dental pain, rhinitis, cancer pain, bladder disorder.

"Pruritus" includes acute pruritus, chronic pruritus, histamine dependent pruritus, histamine independent pruritus.

"Neurogenic inflammation" may be associated with asthma, arthritis, eczema, headache, migraine, or psoriasis, or a combination thereof.

"Cough" includes pathological or chronic cough.

Effective dose is selected in the range of 0.01 mg to 100 mg per 1 kg of body weight per one time. Alternatively, a dose of 5 to 5000 mg, preferably a dose of 10 to 500 mg per a patient may be selected. However, a dose of the pharmaceutical composition containing the monoclonal antibody or the antibody fragment thereof of the present invention is not limited to these doses. Administering duration may be also appropriately selected depending on the age, symptom and the like of the patient. The pharmaceutical composition of the present invention may also include a pharmaceutically acceptable carrier or additive as well depending on the route of administration. Examples of such carrier and additive include water, pharmaceutically acceptable organic solvent, collagen, polyvinyl alcohol, polyvinylpyrrolidone, sodium alginate, water-soluble dextran, pectin, methyl cellulose, ethyl cellulose, casein, diglycerin, propylene glycol, polyethylene glycol, Vaseline, human serum albumin (HSA), mannitol, sorbitol, lactose, and surfactants permitted as a pharmaceutical additive. An additive for use is appropriately selected or combined from the above depending on the dose form, but it is not limited thereto.

The present invention comprises a polynucleotide encoding the heavy and/or light chain variable regions of a monoclonal antibody of the present invention. A polynucleotide encoding the heavy chain variable regions of a monoclonal antibody of the present invention may further encode the heavy chain constant regions. A polynucleotide encoding the light chain variable regions of a monoclonal antibody of the present invention may further encodes light chain constant regions. The present invention also includes expression vectors containing at least one of these polynucleotides.

The polynucleotide is polymer consisting of nucleotide such as several deoxyribonucleic acid (DNA) or ribonucleic acid (RNA), so far as it encodes antibody of the present invention. These may include bases other than natural products. The polynucleotide of the present invention is available for producing antibodies in a manner of genetic technology, and it is useful as probe for the screening of antibodies having equivalent activity with the antibody of the present invention. That is, by using polynucleotide encoding antibody of the present invention or a part thereof as probe and applying technique such as hybridization or gene amplification technique such as PCR, DNA which can hybridize with said polynucleotide in the stringent condition and encodes antibody having equivalence activity with antibody of the present invention, is obtainable. Such these DNA are also embraced in the polynucleotide of the present invention.

Hybridization technique (Sambrook, J et al., Molecular Cloning 2nd ed., 9.47-9.58, Cold Spring Harbor Lab. press, 1989) is the well-known art for the skilled person. The condition for hybridization, for example, includes low-stringent condition. The low-stringent condition means washing step after hybridization is carried on under, for example, 0.1×SSC containing 0.1% SDS at 42° C., preferably 0.1×SSC containing 0.1% SDS at 50° C. More preferable hybridization condition is high-stringent. High-stringent condition means for example, under 5×SSC containing 0.1% SDS at 65° C. Under these conditions, with higher temperature, higher similarity polynucleotide is expected to be obtained efficiently. As a factor affecting stringency for hybridization, several factors such as temperature, or salt concentration, are recited. The skilled person can select these factors appropriately and can have a similar stringency.

Antibodies, functionally equivalent to the monoclonal antibody of the present invention, have generally high similarity in the amino acid sequence. These antibodies are encoded by polynucleotide, which are obtained with above described hybridization or gene amplification techniques. The antibodies, which are functionally equivalent to the antibody of the present invention and have high similarity in the amino acid sequence of the antibodies, are embraced by the present invention. High similarity means the similarity of at least more than 75% in the amino acid sequence, preferably the similarity of 85%, and more preferably the similarity of 95%. To determine the similarity of the polypeptide, algorithm described in the literature (Wilbur, W. J. and Lipman, D. J. Proc. Natl. Acad. Sci. USA (1983) 80, 726-730) is available.

The monoclonal antibody or its antibody fragment of the present invention specifically binds to Nav1.7, so it can be used to detect Nav1.7 in biological samples. Biological samples include blood, plasma, serum, urine, organs, tissues, bone marrow, lymph nodes, and the like. Therefore, a kit including a monoclonal antibody of the present invention is available as a kit for detecting Nav1.7. This kit includes a monoclonal antibody or its antibody fragment of the present invention, and may also include a labeled secondary antibody, a substrate required to detect labels, a carrier, a washing buffer, a sample dilution, an enzyme substrate, a reaction stop solution, Nav1.7 protein as a purification standard substrate, instructions for use, and the like.

EXAMPLE

Hereinafter, the present invention will be specifically described with reference to Examples. However, the present invention is not limited by Examples given below.

Example 1: Preparation of an Antibody Against Nav1.7

A peptide (1418-SVNVDKQPKYEYSL (SEQ ID NO: 1)-1431; hCE3C peptides) corresponding to domain C and E3 extracellular loop C terminal regions of human Nav1.7 (UniProtKB/Swiss-Prot:Q15858) was selected as an antigen.

A peptide (Cys-SVNVDKQPKYEYSL (SEQ ID NO: 1); Cys-hCE3C) to which a Cys residue was added at the N-terminal end was synthesized (manufactured by Toray Corporation). The peptide was bound to maleimidated giant keyhole limpets hemocyanin (manufactured by Thermo Scientific Corporation) to prepare an immunogen. This peptide-KLH complex was immunized with Freund's complete adjuvant to A/J Jms S1c female mice. Additional immunization with Freund's incomplete adjuvant were then performed four times.

Three days after the final immunization, the spleen was excised. The spleen cell and the mouse myeloma cell (p3x6363-Ag8., Tokyo-based Mass Laboratory) were fused by the PEG-method and selected in medium containing hypoxanthine, aminopterin and thymidine. A hybridoma producing bound antibodies was established by ELISA methods using immunogenic peptides with the culture supernatant.

Example 2: Determination of Antibody Sequences

The amino acid sequences of the heavy and light chain variable regions of the antibody, were determined from hybridoma cells of established clones by conventional methods (Table 1).

TABLE 1

| mAb | variable regions | SEQ ID | | SEQ ID | variable regions | SEQ ID | | SEQ ID |
|---|---|---|---|---|---|---|---|---|
| 3B2 | heavy chain | 2 | CDR1 | 3 | light chain | 33 | CDR1 | 34 |
| | | | CDR2 | 4 | | | CDR2 | 35 |
| | | | CDR3 | 5 | | | CDR3 | 36 |
| 5E12 | heavy chain | 6 | CDR1 | 7 | light chain | 37 | CDR1 | 38 |
| | | | CDR2 | 8 | | | CDR2 | 39 |
| | | | CDR3 | 9 | | | CDR3 | 40 |
| 7B9 | heavy chain | 10 | CDR1 | 11 | light chain | 41 | CDR1 | 38 |
| | | | CDR2 | 12 | | | CDR2 | 42 |
| | | | CDR3 | 13 | | | CDR3 | 40 |
| 15C8 | heavy chain | 14 | CDR1 | 15 | light chain | 43 | CDR1 | 34 |
| | | | CDR2 | 16 | | | CDR2 | 35 |
| | | | CDR3 | 17 | | | CDR3 | 36 |
| 15H6 | heavy chain | 18 | CDR1 | 15 | light chain | 44 | CDR1 | 34 |
| | | | CDR2 | 19 | | | CDR2 | 45 |
| | | | CDR3 | 17 | | | CDR3 | 36 |
| 28B5 | heavy chain | 20 | CDR1 | 21 | light chain | 46 | CDR1 | 34 |
| | | | CDR2 | 22 | | | CDR2 | 35 |
| | | | CDR3 | 17 | | | CDR3 | 47 |
| 29G3 | heavy chain | 23 | CDR1 | 15 | light chain | 48 | CDR1 | 34 |
| | | | CDR2 | 24 | | | CDR2 | 35 |
| | | | CDR3 | 25 | | | CDR3 | 36 |
| 12H4 | heavy chain | 26 | CDR1 | 27 | light chain | 49 | CDR1 | 34 |
| | | | CDR2 | 28 | | | CDR2 | 35 |
| | | | CDR3 | 29 | | | CDR3 | 50 |

TABLE 1-continued

| mAb | variable regions | SEQ ID | | SEQ ID | variable regions | | SEQ ID | | SEQ ID |
|---|---|---|---|---|---|---|---|---|---|
| 22D3 | heavy chain | 30 | CDR1 | 31 | light chain | 51 | CDR1 | | 34 |
| | | | CDR2 | 32 | | | CDR2 | | 35 |
| | | | CDR3 | 29 | | | CDR3 | | 50 |
| 3B2/28B5 | heavy chain | 2 | CDR1 | 3 | light chain | 46 | CDR1 | | 34 |
| | | | CDR2 | 4 | | | CDR2 | | 35 |
| | | | CDR3 | 5 | | | CDR3 | | 47 |
| 3B2/15C8 | heavy chain | 2 | CDR1 | 3 | light chain | 43 | CDR1 | | 34 |
| | | | CDR2 | 4 | | | CDR2 | | 35 |
| | | | CDR3 | 5 | | | CDR3 | | 36 |
| 28B5/15C8 | heavy chain | 20 | CDR1 | 21 | light chain | 43 | CDR1 | | 34 |
| | | | CDR2 | 22 | | | CDR2 | | 35 |
| | | | CDR3 | 17 | | | CDR3 | | 36 |

Example 3: Alignment of Antibody Sequences

The amino acid sequences of the heavy and light chains of 15C8, 15H6, 28B5 and 29G3 were subjected to Kabat numbering using the antibody-sequence analysis software abYsis and alignment by the gene-analysis software GENETIX (FIGS. 1 and 2). As a result, amino acid sequences of 15C8, 15H6, 28B5 and 29G3 were similar as described below.

CDR1 of the light chain was composed of 16 amino acids of SEQ ID NO:34.

CDR2 of the light chain was composed of the seven amino acids of K-V-S-N-R-Xaa1-S, wherein Xaa1 was F or I: SEQ ID NO:54.

CDR3 of the light chain was composed of 9 amino acids of S-Q-S-Xaa2-H-V-P-Xaa3-T, wherein Xaa2 was T or I and Xaa3 was F or W: SEQ ID NO: 55.

CDR1 of the heavy chain was composed of the 5 amino acids of G-Y-Y-Xaa4-H, wherein Xaa4 was M or I: SEQ ID NO: 56.

CDR2 of the heavy chain was composed of 17 amino acids of L-I-I-P-Y-Xaa5-G-Xaa6-Xaa7-F-Y-N-Xaa8-K-F-Xaa9-G, wherein Xaa5 was S or N, Xaa6 is D or E, Xaa7 was T or 1, Xaa8 is Q or P, and Xaa9 is K or R: SEQ ID NO:57.

CDR3 of the heavy chain was composed of the 9 amino acids of A-Xaa10-V-S-Y-A-M-D-Y, wherein Xaa10 was E or D: SEQ ID NO:58.

Example 4: Humanization of Antibody

12H4 was humanized by the following method. Human germline acceptor sequences, similar to the V gene domain sequences of the heavy and light chains in amino acid sequences of the murine antibody, were searched and selected by sequence analysis software Absis. For J-chain regions, highly homologous sequences to DNA sequences of the murine antibody were searched by IMGT (http://www.imgt.org/) to obtain a human framework sequence. The humanized antibody sequence listed in Table 2 was designed by implanting CDR1, CDR2, and CDR3 on the mouse antibody heavy and light chains to this human framework sequence, as defined by Kabat numbering (Wu, T. T. and Kabat, E. A., J Exp. Med. August 1; 132(2):211-50. (1970)). As the constant region of h12H4, h12H4-2 and h12H4-3, hIgG4Pro (SEQ ID NO: 62) or hIgG1 (SEQ ID NO: 63) was used for the heavy chain and hIgK (SEQ ID NO: 64) was used for the light chain.

A humanized 12H4 (h12H4), and h12H4-2 and h12H4-3 implanted with CDRs to other human germline acceptor sequences, showed similar affinities to a mouse antibody against immunogenic peptide (Cys-CE3C) in the manner described in Example 5.

TABLE 2

| mAb | variable regions | SEQ ID | | SEQ ID | variable regions | | SEQ ID | | SEQ ID |
|---|---|---|---|---|---|---|---|---|---|
| h12H4 | heavy chain | 52 | CDR1 | 27 | light chain | 53 | CDR1 | | 34 |
| | | | CDR2 | 28 | | | CDR2 | | 35 |
| | | | CDR3 | 29 | | | CDR3 | | 50 |
| h12H4-2 | heavy chain | 59 | CDR1 | 27 | light chain | 53 | CDR1 | | 34 |
| | | | CDR2 | 28 | | | CDR2 | | 35 |
| | | | CDR3 | 29 | | | CDR3 | | 50 |
| h12H4-3 | heavy chain | 60 | CDR1 | 27 | light chain | 61 | CDR1 | | 34 |
| | | | CDR2 | 28 | | | CDR2 | | 35 |
| | | | CDR3 | 29 | | | CDR3 | | 50 |

Example 5: Affinity Assessment

The affinity for immunogenic peptides (Cys-hCE3C) was determined by the competitive ELISA method described below.

A dilute solution of the obtained mouse antibody was added to an anti-mouse IgG antibody immobilized plate and allowed to bind with room temperature for 3 hours. After washing three times with a cleaning buffer for ELISA, a biotin-labeled immunogenic peptide and Streptavidin-HRP (manufactured by PIERCE) were added. Simultaneously, a dilution series of unlabeled immunogenic peptide was added and reacted overnight at 4° C. After washing three times with ELISA wash, TMB-Substrate Chromogen (manufactured by Thermo Fisher Scientific) was added to color. The reaction was quenched with an equal volume of 0.05N sulfuric acid, and absorbance at 450 nm was measured. Concentration of an unlabeled peptide which attenuated the signal of biotin-labeled peptide by half was taken as IC50. As a result, it showed a strong affinity to the immune peptide as shown in Table 3.

TABLE 3

| mAb | IC50 (nM) |
|---|---|
| 3B2 | 9.5 |
| 15C8 | 6.3 |
| 29G3 | 7.0 |
| 12H4 | 0.3 |
| h12H4 | 0.4 |
| h12H4-2 | 0.5 |
| h12H4-3 | 0.5 |

Example 6: Identification of Critical Amino Acids for Humanized 12H4 Binding

For humanized 12H4 (h12H4), numbering of Kabat and definition of CDRs were performed by an antibody-sequence analysis software abYsis. The results are shown in FIG. 3A, 3B. In addition, a mutant in which a point mutation was introduced into an amino acid corresponding to CDRs was produced, and the affinity was calculated by the methodology described in Example 5. At this time, a peptide (SVNVDKQPKYEYSL; SEQ ID NO: 1) excluding the N-terminal Cys of the immunogen peptide was used as the unlabeled peptide, and the affinity for this peptide was calculated. The light chain results are shown in Table 4, and the heavy chain results are shown in Table 5. As a result, the light chain Q90 and V94 lost its affinity for this peptide when it was replaced by another amino acid. In Table 4, n.d. means undetectable. This suggests that Q90 and V94 of the light chain are particularly important amino acids for binding. And, the affinity of N28 of the light chain and M99 of the heavy chain dropped more than 10 times, when the amino acid was replaced with the other amino acid. From this fact, N28 of the light chain and M99 of the heavy chain are considered to be the important amino acids for binding.

TABLE 4

| | mutant | IC50 ratio (mutant/wt) |
|---|---|---|
| CDR1 | R24K | 0.8 |
| | S25T | 0.8 |
| | S26T | 1.3 |
| | Q27N | 1.5 |
| | S27aT | 1.3 |
| | L27bI | 1.8 |
| | V27cL | 1.4 |
| | H27dR | 2.1 |
| | S27eT | 1.0 |
| | N28Q | 10.0 |
| | G29A | 0.8 |
| | N30Q | 1.0 |
| | T31S | 1.0 |
| | Y32F | 3.9 |
| | L33I | 0.9 |
| | H34R | 1.3 |
| CDR2 | K50R | 1.5 |
| | V51L | 1.6 |
| | S52T | 1.3 |
| | N53Q | 1.4 |
| | R54K | 1.4 |
| | F55L | 2.3 |
| | S56T | 1.5 |
| CDR3 | S89T | 1.4 |
| | Q90N | n.d. |
| | S91T | 2.3 |

TABLE 4-continued

| | mutant | IC50 ratio (mutant/wt) |
|---|---|---|
| | T92S | 1.3 |
| | H93R | 2.4 |
| | V94L | n.d. |
| | P95Gz | 1.5 |
| | W96Y | 2.4 |
| | T97S | 1.4 |

TABLE 5

| | mutant | IC50 ratio (mutant/wt) |
|---|---|---|
| CDR1 | Y31F | 0.6 |
| | Y32F | 0.8 |
| | Y33F | 1.0 |
| | I34L | 0.9 |
| | Q35N | 1.3 |
| CDR2 | W50Y | 2.0 |
| | I51L | 1.7 |
| | Y52aF | 1.4 |
| | P52bG | 1.0 |
| | G53A | 1.1 |
| | N54Q | 1.2 |
| | G55A | 1.3 |
| | N56Q | 1.3 |
| | S57T | 1.2 |
| | N58Q | 1.2 |
| | I59L | 0.9 |
| | T60S | 2.6 |
| | E61D | 1.9 |
| | K62R | 1.8 |
| | F63L | 1.1 |
| | K64R | 2.2 |
| | G65A | 2.5 |
| CDR3 | I95L | 1.2 |
| | F96L | 2.3 |
| | T97S | 2.1 |
| | T98S | 1.6 |
| | M99L | 32.0 |
| | V100L | 0.6 |
| | G100aA | 1.2 |
| | D101E | 1.4 |
| | Y102F | 0.4 |

Example 7: Drug Efficacy Assessment (7-1) Preparation of Rat Partial Sciatic Nerve Ligation Models A rat was anesthetized with isoflurane and the left leg was shaved. The upper thigh skin was incised and the muscles were cut to expose the sciatic nerve. Approximately half of the sciatic nerve was tightly ligated with nylon thread and the muscles and skin were sutured. This was taken as surgery. Similar actions except for sciatic nerve ligation were performed on the right leg as sham surgery.

(7-2) Drug Efficacy Assessment by Local Intraplantar Administration

A rat prepared in (7-1) was used to assess the pain behavior of mechanical hyperalgesia by analgesiometer (the method of Randal Selitto) two weeks after surgery. The rat hindlimb was compressed so that the stimulus pressure increased by 16 g per second by analgesiometer, and the pressure when the rat exhibited escape behavior was set as a pain threshold. The pain threshold was assessed for the left and right hind limbs and was set as a pain threshold before treatment. Adopted animals had pain thresholds of 60-90 g on surgery and pain thresholds of 100-175 g on sham surgery. For training animals, similar procedures were performed before measuring the pain thresholds before treatment. An antibody in the present invention was prepared at 300 μg/40 μL using PBS and 40 μL of that was intraplantarly administrated. Five minutes after administration, the pain threshold of the right and left hind limbs were assessed and set as a pain threshold after treatment. % reversal values were calculated by the methods described below to evaluate the pain effects of the antibodies.

% reversal values=(a pain threshold after treatment on the surgery–a pain threshold before treatment on surgery)/(a pain threshold after treatment on sham surgery–a pain threshold after treatment on sham surgery)×100

The results of 3B2, 15C8, 29G3 and 12H4 are shown in FIG. 4. An antibody of the present invention inhibited Nav1.7 by the intraplantar administration and showed significant efficacy of pain behavior.

(7-3) Evaluation of Drug Efficiency by Intravenous Administration

A rat prepared in (7-1) was used to assess the behavior of mechanical allodynia by a von Frey filament two weeks after surgery. The rat was placed in a plastic cage on a wire mesh to acclimate. After antibody administration, the von Frey filaments (0.4-26 g) were pressed to the paw of the rat from the wire mesh side. The rat started to show the escape behavior at a pressure value of the filament. The value was set as a pain threshold. The threshold was assessed for the left and right hind paws and was set as a pain threshold before treatment. Adopted animals had pain thresholds of 0.6-2 g on surgery and pain thresholds of 8-15 g on sham surgery. For training animals, similar procedures were performed before measuring the pain threshold before treatment. An antibody of the present invention was prepared at 50 mg/kg using saline and was intravenously administrated. From 0.5 to 72 hours after administration, the pain threshold of the right and left hind paws. It was set as a pain threshold after treatment. % reversal values were calculated by the methods described below to evaluate the pain effects of the compound.

% reversal values=(a logarithm of a pain threshold after treatment on surgery–a logarithm of a pain threshold before treatment on surgery)/(a logarithm of a pain threshold after treatment on sham surgery–a logarithm of a pain threshold after treatment on sham surgery)

Figure 5:
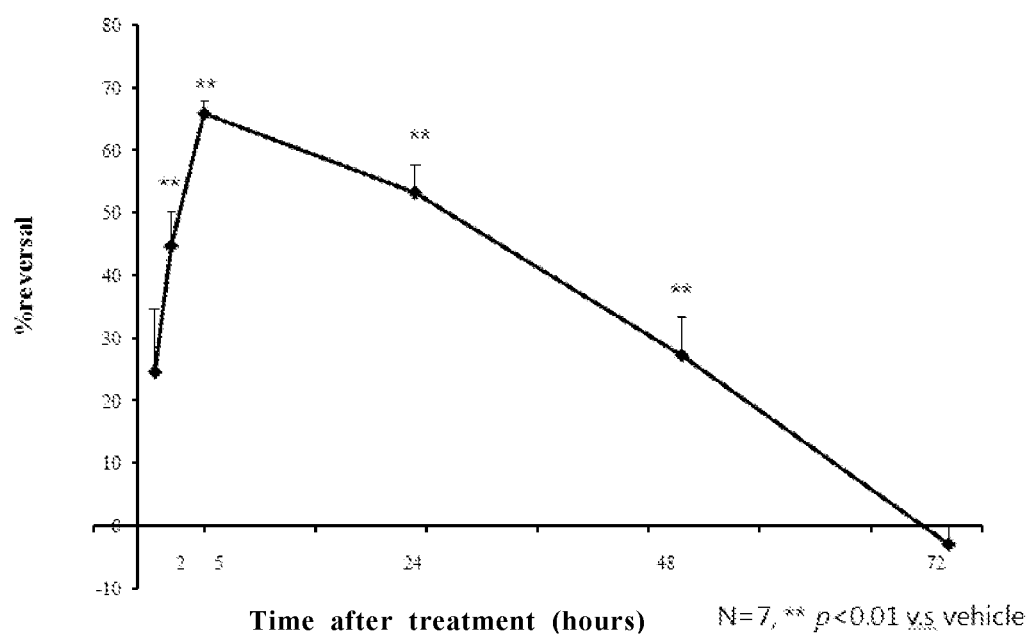

The result of humanized 12H4 (h12H4) is shown as FIG. 5. An antibody of the present invention showed significant drug efficacy of pain behavior by the intravenous administration.

INDUSTRIAL APPLICABILITY

A monoclonal antibody or its antibody fragment of the present invention may be used to detect Nav1.7 in biological samples. In addition, a pharmaceutical composition comprising a monoclonal antibody or its antibody fragment of the present invention, is great useful as a medicine for treating or preventing Nav1.7 related diseases.

The invention claimed is:

1. A antibody that binds to Nav1.7 or antibody fragment thereof, comprising:
   a heavy chain variable region including a CDR1 having the amino acid sequence of SEQ ID NO: 21, a CDR2 having the amino acid sequence of SEQ ID NO: 22 and a CDR3 having the amino acid sequence of SEQ ID NO: 17, or a CDR1 having the amino acid sequence of SEQ ID NO: 3, a CDR2 having the amino acid sequence of SEQ ID NO: 4 and a CDR3 having the amino acid sequence of SEQ ID NO: 5, and a light chain variable region including a CDR1 having the amino acid sequence of SEQ ID NO: 34, a CDR2 having the amino acid sequence of SEQ ID NO: 35 and a CDR3 having the amino acid sequence of SEQ ID NO: 47;
   a heavy chain variable region including a CDR1 having the amino acid sequence of SEQ ID NO: 27, a CDR2 having the amino acid sequence of SEQ ID NO: 28 and a CDR3 having the amino acid sequence of SEQ ID NO: 29, and a light chain variable region including a CDR1 having the amino acid sequence of SEQ ID NO: 34, a CDR2 having the amino acid sequence of SEQ ID NO: 35 and a CDR3 having the amino acid sequence of SEQ ID NO: 50;
   a heavy chain variable region including a CDR1 having the amino acid sequence of SEQ ID NO: 3, a CDR2 having the amino acid sequence of SEQ ID NO: 4 and a CDR3 having the amino acid sequence of SEQ ID NO: 5, a CDR1 having the amino acid sequence of SEQ ID NO: 15, a CDR2 having the amino acid sequence of SEQ ID NO: 16 and a CDR3 having the amino acid sequence of SEQ ID NO: 17, a CDR1 having the amino acid sequence of SEQ ID NO: 15, a CDR2 having the amino acid sequence of SEQ ID NO: 24 and a CDR3 having the amino acid sequence of SEQ ID NO: 25, or a CDR1 having the amino acid sequence of SEQ ID NO: 21, a CDR2 having the amino acid sequence of SEQ ID NO: 22 and a CDR3 having the amino acid sequence of SEQ ID NO: 17, and a light chain variable region including a CDR1 having the amino acid sequence of SEQ ID NO: 34, a CDR2 having the amino acid sequence of SEQ ID NO: 35 and a CDR3 having the amino acid sequence of SEQ ID NO: 36;
   a heavy chain variable region including a CDR1 having the amino acid sequence of SEQ ID NO: 7, a CDR2 having the amino acid sequence of SEQ ID NO: 8 and a CDR3 having the amino acid sequence of SEQ ID NO: 9, and a light chain variable region including a CDR1 having the amino acid sequence of SEQ ID NO: 38, a CDR2 having the amino acid sequence of SEQ ID NO: 39 and a CDR3 having the amino acid sequence of SEQ ID NO: 40;
   a heavy chain variable region including a CDR1 having the amino acid sequence of SEQ ID NO: 11, a CDR2 having the amino acid sequence of SEQ ID NO: 12 and a CDR3 having the amino acid sequence of SEQ ID NO: 13, and a light chain variable region including a CDR1 having the amino acid sequence of SEQ ID NO: 38, a CDR2 having the amino acid sequence of SEQ ID NO: 42 and a CDR3 having the amino acid sequence of SEQ ID NO: 40;

a heavy chain variable region including a CDR1 having the amino acid sequence of SEQ ID NO: 15, a CDR2 having the amino acid sequence of SEQ ID NO: 19 and a CDR3 having the amino acid sequence of SEQ ID NO: 17, and a light chain variable region including a CDR1 having the amino acid sequence of SEQ ID NO: 34, a CDR2 having the amino acid sequence of SEQ ID NO: 45 and a CDR3 having the amino acid sequence of SEQ ID NO: 36; or a heavy chain variable region including a CDR1 having the amino acid sequence of SEQ ID NO: 31, a CDR2 having the amino acid sequence of SEQ ID NO: 32 and a CDR3 having the amino acid sequence of SEQ ID NO: 29, and a light chain variable region including a CDR1 having the amino acid sequence of SEQ ID NO: 34, a CDR2 having the amino acid sequence of SEQ ID NO: 35 and a CDR3 having the amino acid sequence of SEQ ID NO: 50.

2. The antibody that binds to Nav1.7 or antibody fragment thereof according to claim 1, wherein the antibody or antibody fragment thereof has:
   the heavy chain variable region having the amino acid sequence of SEQ ID NO: 52, and the light chain variable region having the amino acid sequence of SEQ ID NO: 53;
   the heavy chain variable region having the amino acid sequence of SEQ ID NO: 59, and the light chain variable region having the amino acid sequence of SEQ ID NO: 53; or
   the heavy chain variable region having the amino acid sequence of SEQ ID NO: 60, and the light chain variable region having the amino acid sequence of SEQ ID NO: 61.

3. The antibody that binds to Nav1.7 or antibody fragment thereof according to claim 1, further comprising:
   a heavy chain constant region having the amino acid sequence of SEQ ID NO: 62 or 63, and the light chain constant region having the amino acid sequence of SEQ ID NO: 64.

4. A pharmaceutical composition, comprising:
   the antibody that binds to Nav1.7 or antibody fragment thereof according to claim 1.

5. A method for treating pain, comprising: administering the pharmaceutical composition of claim 4 to a patient in need thereof.

6. A polynucleotide, wherein the polynucleotide encodes the heavy chain variable region of the antibody of claim 2.

7. The polynucleotide according to claim 6, wherein the polynucleotide encodes the heavy chain constant region of the antibody of claim 3.

8. A polynucleotide, wherein the polynucleotide encodes the light chain variable region of the antibody of claim 2.

9. The polynucleotide according to claim 8, wherein the polynucleotide encodes the light chain constant region of the antibody of claim 3.

10. An expression vector, comprising:
    the polynucleotide of claim 6.

11. An expression vector, comprising:
    the polynucleotide of claim 7.

12. An expression vector, comprising:
    the polynucleotide of claim 8.

13. An expression vector, comprising:
    the polynucleotide of claim 9.

14. A pharmaceutical composition, comprising:
    the antibody that binds to Nav1.7 or antibody fragment thereof according to claim 2.

15. A method for treating pain, comprising:
    administering the pharmaceutical composition of claim 14 to a patient in need thereof.

16. A pharmaceutical composition, comprising:
    the antibody that binds to Nav1.7 or antibody fragment thereof according to claim 3.

17. A method for treating pain, comprising:
    administering the pharmaceutical composition of claim 16 to a patient in need thereof.

18. The antibody that binds to Nav1.7 or antibody fragment thereof according to claim 2, further comprising:
    a heavy chain constant region having the amino acid sequence of SEQ ID NO: 62 or 63, and the light chain constant region having the amino acid sequence of SEQ ID NO: 64.

19. A pharmaceutical composition, comprising:
    the antibody that binds to Nav1.7 or antibody fragment thereof according to claim 18.

20. A method for treating pain, comprising:
    administering the pharmaceutical composition of claim 19 to a patient in need thereof.

* * * * *